(12) United States Patent
Quinn

(10) Patent No.: US 7,220,274 B1
(45) Date of Patent: May 22, 2007

(54) INTRAVASCULAR STENT GRAFTS AND METHODS FOR DEPLOYING THE SAME

(76) Inventor: Stephen F. Quinn, 3365 Bardell Ave., Eugene, OR (US) 97401

( * ) Notice: Subject to any disclaimer, the term of this patent is extended or adjusted under 35 U.S.C. 154(b) by 661 days.

(21) Appl. No.: 10/393,565

(22) Filed: Mar. 21, 2003

(51) Int. Cl.
*A61F 2/06* (2006.01)

(52) U.S. Cl. ..................................... 623/1.13

(58) Field of Classification Search ............... 623/1.11, 623/1.12, 1.13, 1.16, 1.23, 1.27; 606/191, 606/192, 194, 198
See application file for complete search history.

(56) References Cited

U.S. PATENT DOCUMENTS

| | | | |
|---|---|---|---|
| 5,282,824 | A | 2/1994 | Gianturco |
| 5,316,023 | A | 5/1994 | Palmaz et al. |
| 5,443,496 | A | 8/1995 | Schwartz et al. |
| 5,562,697 | A | 10/1996 | Christiansen |
| 5,571,170 | A | 11/1996 | Palmaz et al. |
| 5,591,195 | A | 1/1997 | Taheri et al. |
| 5,628,787 | A | 5/1997 | Mayer |
| 5,693,084 | A | 12/1997 | Chuter |
| 5,728,131 | A * | 3/1998 | Frantzen et al. ............ 623/1.13 |
| 5,755,778 | A | 5/1998 | Kleshinski |
| 5,824,040 | A | 10/1998 | Cox et al. |
| 5,851,228 | A | 12/1998 | Pinheiro |
| 5,855,598 | A | 1/1999 | Pinchuk |
| 5,893,887 | A | 4/1999 | Jayaraman |
| 5,906,641 | A | 5/1999 | Thompson et al. |
| 5,957,974 | A | 9/1999 | Thompson et al. |
| 5,972,023 | A | 10/1999 | Tanner et al. |
| 6,093,203 | A | 7/2000 | Uflacker |
| 6,129,756 | A | 10/2000 | Kugler et al. |
| 6,210,429 | B1 | 4/2001 | Vardi et al. |
| 6,319,278 | B1 | 11/2001 | Quinn |
| 6,344,056 | B1 | 2/2002 | Dehdashtian |
| 6,355,056 | B1 | 3/2002 | Pinheiro |
| 6,656,214 | B1 * | 12/2003 | Fogarty et al. ............ 623/1.13 |

FOREIGN PATENT DOCUMENTS

JP 279532 10/2000

OTHER PUBLICATIONS

U.S. Appl. No. 10/277,641, filed Oct. 22, 2002, Quinn.
U.S. Appl. No. 09/734,987, filed Dec. 11, 2000, Quinn.

(Continued)

*Primary Examiner*—Kevin Truong
(74) *Attorney, Agent, or Firm*—David S. Alavi

(57) ABSTRACT

A stent graft comprises two stent segments connected to open ends of a graft, arranged along the length thereof without overlap, reducing the transverse size and facilitating deployment. It may include longitudinal struts, sliding stent, additional stent segments, removable stent(s), etc. Various methods are employed for deployment.

Other stent graft deploying methods comprise independently introducing and maneuvering graft and stent segments to the repair site from one or more introduction sites, and assembling the stent graft at the repair site. Intravascular and/or extravascular deployment hardware may be employed. Additional sealing and/or structural stent segments may be deployed. Branched grafts may be deployed. Removable stent segment(s) may be employed for positioning the graft and then later removed.

A stent anastomosis for securing/sealing a graft end is disclosed. A branched stent graft including two branch stent grafts deployed side-by-die within a main stent graft is disclosed.

18 Claims, 21 Drawing Sheets

OTHER PUBLICATIONS

Stephen F. Quinn MD et al, "Percutaneous Placement of a Low-profile Stent-Graft Device for Aortic Dissections", J. Vasc. Interv. Radiol., vol. 13(8) pp. 791-798 (Aug. 2002).

Shoiji Sakaguchi MD et al, "Twin-tube Endografts for Aortic Aneurysms: An Experimental Feasibility Study", J. Vasc. Interv. Radiol., vol. 10(8) pp. 1092-1098 (1999).

* cited by examiner

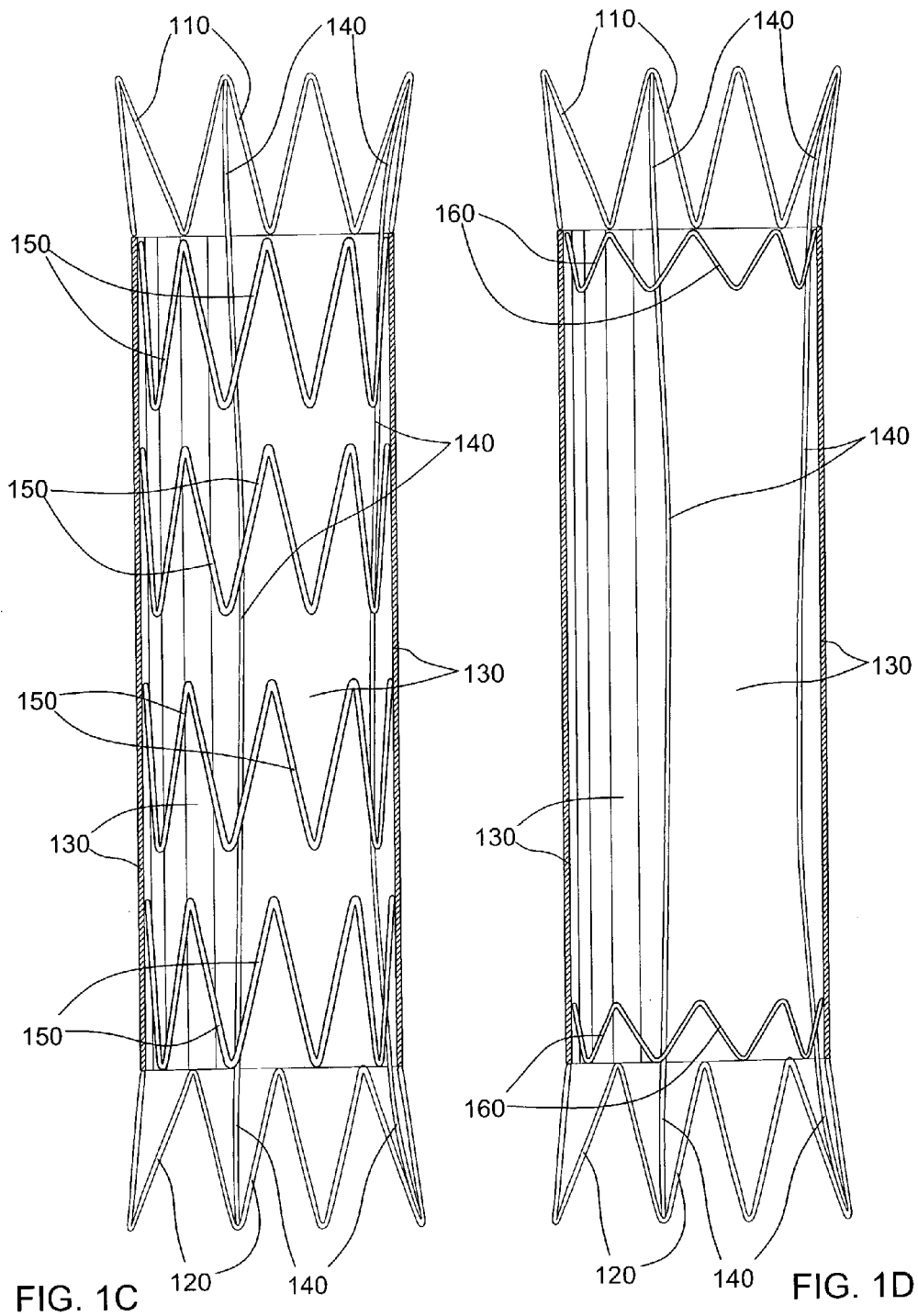

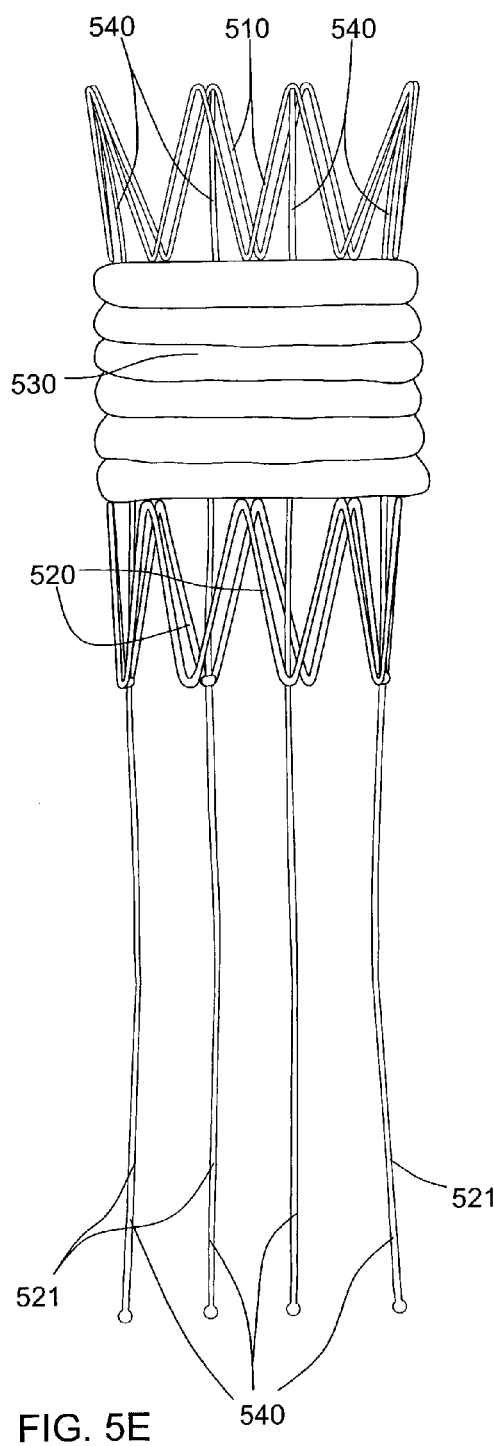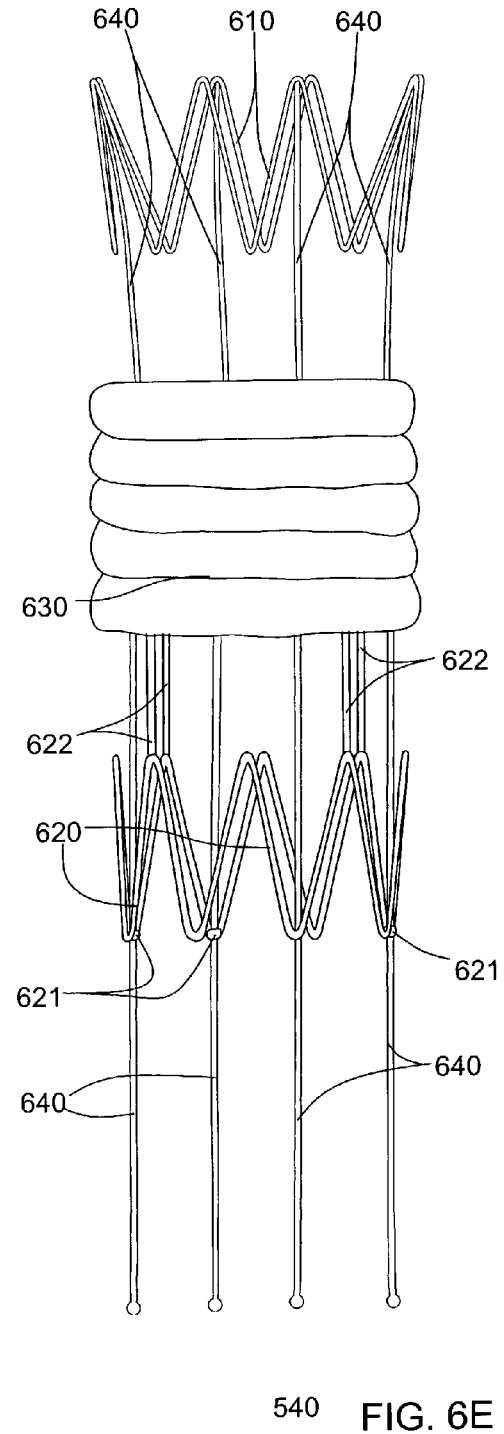
FIG. 5E
FIG. 6E

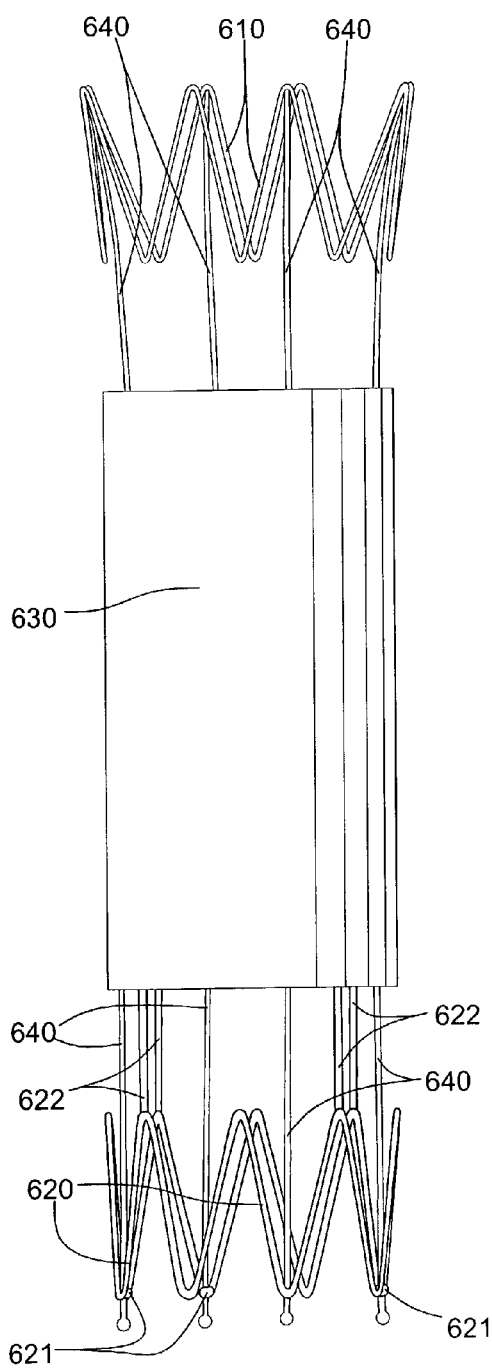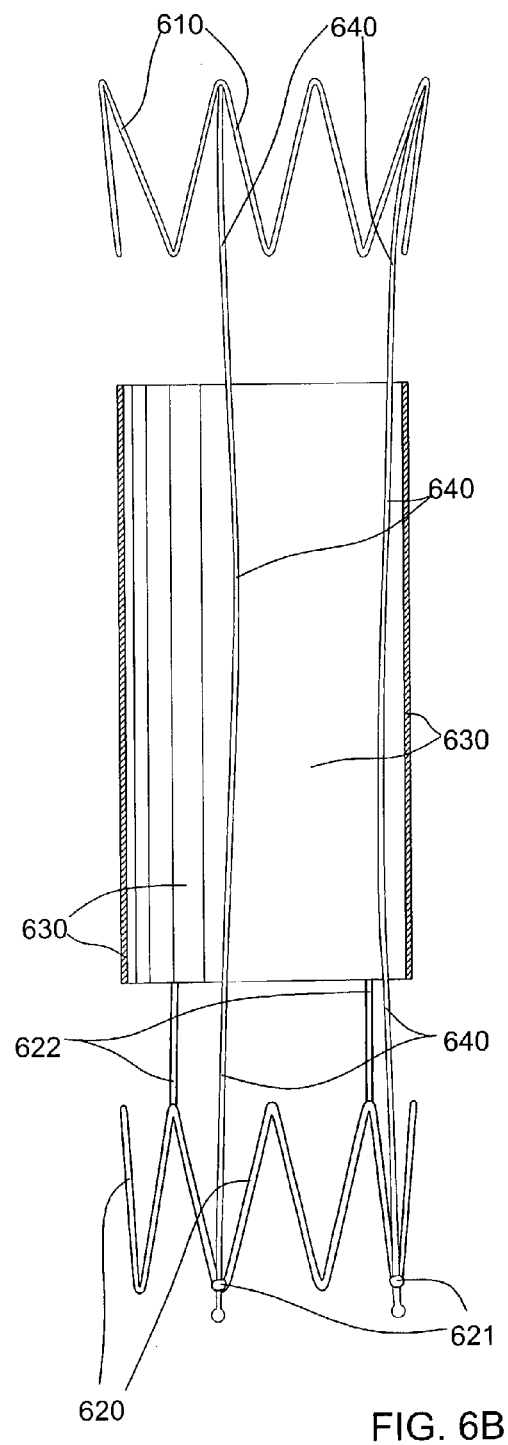
FIG. 6A
FIG. 6B

INTRAVASCULAR STENT GRAFTS AND METHODS FOR DEPLOYING THE SAME

BACKGROUND

This application is related to subject matter disclosed in:

U.S. Pat. No. 6,319,278 entitled "Low profile device for the treatment of vascular abnormalities" issued Nov. 20, 2001 in the name of Stephen F. Quinn, said patent being hereby incorporated by reference as if fully set forth herein;

U.S. non-provisional application Ser. No. 10/277,641 entitled "Bifurcated side-access intravascular stent graft" filed Oct. 22, 2002 in the name of Stephen F. Quinn, said application being hereby incorporated by reference as if fully set forth herein;

U.S. non-provisional application Ser. No. 09/734,987 entitled "Bifurcated side-access intravascular stent graft" filed Dec. 11, 2000 in the name of Stephen F. Quinn (now U.S. Pat. No. 6,645,242), said application being hereby incorporated by reference as if fully set forth herein; and Stephen F. Quinn MD et al, "Percutaneous Placement of a Low-profile Stent-Graft Device for Aortic Dissections", J. Vasc. Interv. Radiol., Vol. 13(8) pp. 791–798 (August 2002).

This application is also related to subject matter disclosed in:

U.S. Pat. No. 5,282,824 entitled "Percutaneous stent assembly" issued Feb. 1, 1994 to Gianturco;

U.S. Pat. No. 5,316,023 entitled "Method for bilateral intra-aortic bypass" issued May 31, 1994 to Palmaz et al;

U.S. Pat. No. 5,443,496 entitled "Intravascular radially expandable stent" issued Aug. 22, 1995 to Schwartz et al;

U.S. Pat. No. 5,562,697 entitled "Self-expanding stent assembly and methods for the manufacture thereof" issued Oct. 8, 1996 to Christiansen;

U.S. Pat. No. 5,571,170 entitled "Method and apparatus for bilateral intra-aortic bypass" issued Nov. 5, 1996 to Palmaz et al;

U.S. Pat. No. 5,591,195 entitled "Apparatus and method for engrafting a blood vessel" issued Jan. 7, 1997 to Taheri et al;

U.S. Pat. No. 5,628,787 entitled "Clad composite stent" issued May 13, 1997 to Mayer;

U.S. Pat. No. 5,693,084 entitled "Expandable transluminal graft prosthesis for repair of aneurysm" issued Dec. 2, 1997 to Chuter;

U.S. Pat. No. 5,755,778 entitled "Anastomosis device" issued May 26, 1998 to Kleshinski;

U.S. Pat. No. 5,824,040 entitled "Endoluminal prostheses and therapies for highly variable body lumens" issued Oct. 20, 1998 to Cox et al;

U.S. Pat. No. 5,851,228 entitled "Implantable intraluminal prosthesis" issued Dec. 22, 1998 to Pinheiro;

U.S. Pat. No. 5,855,598 entitled "Expandable supportive branched endoluminal grafts" issued Jan. 5, 1999 to Pinchuk;

U.S. Pat. No. 5,893,887 entitled "Stent for positioning at junction of bifurcated blood vessel and method of making" issued Apr. 13, 1999 to Jayaraman;

U.S. Pat. No. 5,906,641 entitled "Bifurcated stent graft" issued May 25, 1999 to Thompson et al;

U.S. Pat. No. 5,957,974 entitled "Stent graft with braided polymeric sleeve" issued Sep. 28, 1999 to Thompson et al;

U.S. Pat. No. 5,972,023 entitled "Implantation device for an aortic graft method of treating aortic aneurysm" issued Oct. 26, 1999 to Tanner et al;

U.S. Pat. No. 6,093,203 entitled "Stent or graft support structure for treating bifurcated vessels having different diameter portions and methods of use and implantation" issued Jul. 25, 2000 to Uflacker;

U.S. Pat. No. 6,129,756 entitled "Biluminal endovascualr graft system" issued Oct. 10, 2000 to Kugler et al;

U.S. Pat. No. 6,210,429 entitled "Extendible stent apparatus" issued Apr. 3, 2001 to Vardi et al;

U.S. Pat. No. 6,344,056 entitled "Vascular grafts for bridging a vessel side branch" issued Feb. 5, 2002 to Dehdashtian;

U.S. Pat. No. 6,355,056 entitled "Implantable intraluminal prosthesis" issued Mar. 12, 2002 to Pinheiro;

Shoiji Sakaguchi MD et al, "Twin-tube Endografts for Aortic Aneurysms: An Experimental Feasibility Study", J. Vasc. Interv. Radiol., Vol. 10(8) pp. 1092–1098 (1999).

In many instances of vascular disease, a damaged, weakened, and/or enlarged portion of a blood vessel must be protected from intravascular fluid pressure. Continued exposure to such fluid pressure may result in progression of damage to the affected area and/or vessel failure, accompanied by significant morbidity or even sudden death. A well-established technique for treating such vascular damage is the use of transluminal stent grafts, many different types of which are described in the above-cited references. Stent grafts are typically introduced into intravascular space at an introduction site remote from the repair site, moved through the vascular system to the repair site, and then deployed. In this way vessels may be repaired at sites deep within the body via an introduction site that is more readily accessible, i.e., through a vessel near the body surface, thereby avoiding a major surgical procedure. In many cases access to the intravascular space at the introduction site may be established percutaneously, while in other cases access to the vessel at the introduction site must be established surgically. Primary factors determining whether such remote access may be employed are: the cross sectional sizes of the vessels to be navigated between the introduction site and the repair site relative to the cross sectional sizes of the stent graft and any necessary deployment hardware; and the tortuousness of the vessels to be navigated between the introduction site and the repair site relative to the flexibility and maneuverability of the stent graft and any necessary deployment hardware.

Briefly, a stent graft comprises two major components, a stent and a graft. The stent (one or more) typically takes the form of a somewhat stiff tube-like structure, often comprising perforated or mesh material, inserted into an affected vessel and fixed in place. The stent may serve to maintain a patent vessel lumen, may serve as structural support for the vessel, and/or may serve as an attachment/seal for a graft. A graft typically takes the form of a flexible tube or sleeve which is at least somewhat fluid-tight (although varying degrees of permeability may be desirable for a variety of reasons). When secured within a vessel using stent(s) (a single stent the length of the graft, a pair of stent segments at the ends of the graft, multiple stent segments spaced along the length of the graft, or other suitable arrangement), the graft becomes a surrogate vessel-within-a-vessel, and bears the brunt of the intravascular fluid pressure. It has become common practice to bridge damaged vessel segment using a sufficiently long graft secured within the vessel with one or more stent segment(s).

Difficulties may arise when vessel damage occurs near a vessel branch point. More elaborate, multi-component devices are required to both shield the damaged vessel portion while maintaining blood flow through the main and branch vessels, as described in several of the above-cited references. Further difficulties may arise in areas where multiple branch points lie near one another. Difficulties may arise in accurately securing the stent graft at a particular vessel location, particularly in the vicinity of one or more branch points. Difficulties may arise if the cross-sectional size of the stent graft (and the necessary deployment hardware) is too large and/or too stiff for ready introduction into and navigation through the vascular system, delivery to the repair site, and/or deployment at the repair site. Under the latter conditions, surgical access to the intravascular introduction site may be required, surgical access to the repair site may be required, or deployment of the stent graft may be ruled out entirely. It is often the case that the cross sectional sizes of the vessels is smaller at the introduction site than at the repair site.

SUMMARY

An intravascular stent graft may comprise first and second stent segments, each adapted for engaging an endoluminal surface of a vessel, and a graft connected near its open ends to the stent segments. The stent segments and the graft are arranged along the length of the stent graft so as to substantially eliminate overlap between the stent segments and the graft. The transverse size of the stent graft is thereby reduced, facilitating introduction of the stent graft into and maneuvering thereof through the intravascular space to an intravascular repair site from a remote introduction site. The stent graft may be variously adapted with longitudinal struts connected to one or both stent segment(s), with one of the stent segments sliding along a longitudinal strut, with the stent segment(s) connected directly to the graft or with a gap between the stent segment(s) and the graft. Additional stent segments and/or stent anastomoses may be deployed for securing and/or sealing the graft, and/or for structural support. The first and/or second stent segments may remain deployed, or may be removed after securing/sealing the graft. Various methods may be employed for deploying such intravascular stent grafts.

Other methods for deploying an intravascular stent graft at an intravascular repair site may comprise: 1) inserting the graft into an intravascular space through an introduction site, maneuvering it through the intravascular space to the repair site, and positioning its ends at the repair site; 2) inserting first and second sealing stent segment, independently of the graft and each other, into the intravascular space though one or more introduction site(s), and maneuvering them through the intravascular space to the repair site; 3) securing the ends of the graft within the vessel at the repair site; 4) engaging the sealing stent segments with the ends of the graft to form substantially fluid-tight seals. One or multiple introduction sites may be employed. Intravascular and/or extravascular deployment hardware may be employed. Additional sealing and/or structural stent segments may be deployed. Branched grafts may be deployed. Additional stent segment(s) may be employed for positioning the graft and then removed after securing/sealing the graft. Complex stent graft structures may be constructed at the repair site from smaller, more readily deployed components.

A stent anastomosis comprises a stent segment reconfigurable between a deployment configuration and a deployed configuration, a transverse dimension of the deployed configuration being substantially larger than a transverse dimension of the deployment configuration, the transverse dimension of the deployed configuration being substantially larger than a longitudinal dimension of the deployed configuration, the stent anastomosis being adapted, in the deployed configuration, for engaging an inner surface of an intravascular graft, securing the end of the graft within a vessel, and forming a substantially fluid-tight seal between the graft and an endoluminal surface of the vessel. Such a stent anastomosis may be employed for securing and/or sealing graft ends. A graft end may be sealed by compression between the stent anastomosis and the vessel wall, while the graft end may be secured by one or more securing members protruding radially outward from the stent anastomosis, piercing the graft and the vessel wall.

A branched stent graft comprises a main stent graft and two branch stent grafts. The main stent graft may include a branch opening in addition to its open ends. The branch stent grafts are deployed side-by-side within the main stent graft. Both branch stent grafts may pass out through the open end of the main stent graft. Alternatively, one branch stent graft may pass out through the open end of the main graft, while the other branch stent graft may pass out through the branch opening of the main stent graft. The side-by-side deployment of the branch stent grafts that substantially fill the main graft and form substantially fluid-tight seals with the main graft and with each other.

Objects and advantages of the present invention may become apparent upon referring to the disclosed embodiments as illustrated in the drawings and disclosed in the following written description and/or claims.

BRIEF DESCRIPTION OF DRAWINGS

FIGS. 1A–1D show an exemplary embodiment of a stent graft.

FIGS. 5A–5E show an exemplary embodiment of a stent graft.

FIGS. 6A–6E show an exemplary embodiment of a stent graft.

Figure 1A:
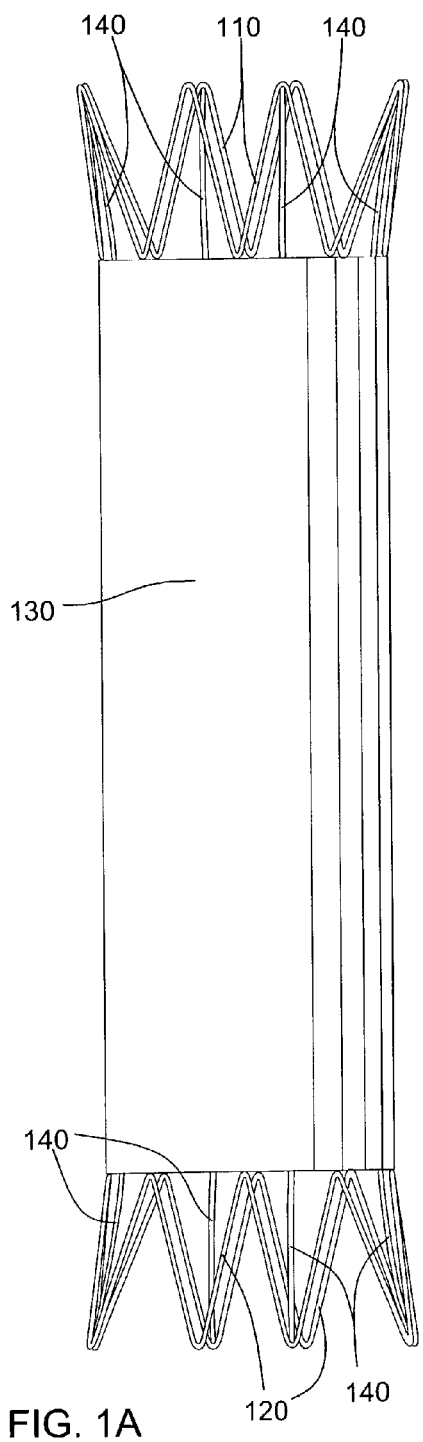

The embodiments shown in the Figures are exemplary, and should not be construed as limiting the scope of the present disclosure and/or appended claims.

DETAILED DESCRIPTION OF EMBODIMENTS

For purposes of the present written description and/or claims, "proximal" shall denote the direction along a vessel system in which multiple smaller vessels come together to form a larger vessel, and "distal" shall denote the opposite direction, i.e., the direction in which a larger vessel divides into multiple smaller vessels. For an arterial system proximal therefore corresponds to "upstream", while distal corresponds to "downstream". It should be noted that for a venous system or a lymphatic system, the correspondence would be reversed. The correspondence may vary for other vascular or duct systems.

Stent grafts as disclosed herein are typically introduced (via percutaneous or surgical access) into intravascular space at a point remote from a vessel repair site, and then moved though one or more vessels to the repair site using various guide wires, sheaths, dilators, pushing and/or pulling devices, and/or other deployment hardware. In addition to the anatomically-defined terms defined in the preceding paragraph (proximal/distal and upstream/downstream), the direction through the vascular system relative to the introduction site must be designated. For purposes of the present written description and/or claims, the "insertion direction" shall be defined as the direction of movement from the introduction site through the vascular system toward the intravascular repair site, while the terms "removal direction" and "withdrawal direction" shall both designate the direction opposite the insertion direction, i.e., the direction of movement from the intravascular repair site through the vascular system toward the introduction site. Similarly, the terms "leading" and "trailing" shall refer to directions along the vessel relative to the introduction and repair sites (the leading end of a device being closer to the repair site as it is maneuvered through the vessels to the repair site; the trailing end being closer to the introduction site). If more than one introduction point is used for a given deployment, then the meanings of insertion direction, removal direction, withdrawal direction, leading, and trailing may vary depending on which of the introduction sites is referred to.

For purposes of the present written description and/or claims, the terms "interior" and "inside" shall denote volume and/or surface(s) within the lumen or passage formed by a stent segment, graft, or combination thereof, while "exterior" and "outside" shall denote volume and/or surfaces without. For purposes of the present written description and/or claims, the terms "inner" and "outer" shall denote longitudinal position along the length of a given stent, graft, or combination stent graft device. "Outer" shall indicate positions toward the ends of the device (first or second end), while "inner" shall refer to positions toward the middle of the length of the device.

Two embodiments of a stent graft are shown in FIGS. 1A–1D and 2A–2D, each embodiment comprising first and second stent segments 110 and 120, and graft 130. Graft 130 comprises an elongated piece of tubular graft material of any suitable type, including but not limited to those disclosed in the above-cited references. Stent segments 110 and 120 may be formed in any suitable configuration using any suitable stent material(s), including but not limited to configurations and materials disclosed in the above-cited references, and are connected by one or more elongated longitudinal strut members 140. Graft 130 is secured between stent segments 110 and 120, either directly thereto (as in FIGS. 1A–1D) or to longitudinal struts 140 leaving a gap between the outer end of the graft 130 and the inner end(s) of the stent segment(s) 110 and/or 120 (as in FIGS. 2A–2D). Stent segments 110 and 120 are left substantially uncovered by graft 130, except perhaps for minimal overlap at points where the graft is connected directly to the stent segment (as in FIGS. 1A–1D, 3A–3D, and 5A–5E). Substantial lack of overlap of the graft and the stent segments enables transverse compression of the stent graft to a smaller cross sectional size than comparable stent grafts with graft material overlapping or covering all or part of one or more of the stent segments. This size reduction may enable percutaneous deployment of the stent graft in clinical situations that may have required surgical access for deployment of previous stent grafts. This size reduction may enable deployment of the stent graft in small and/or tortuous vessels that may have precluded deployment of previous stent grafts.

The longitudinal struts connecting the stent segments may typically comprise one or more stiff longitudinal wires connected at one outer end thereof to stent segment 110 and at the other outer end thereof to stent segment 120. Any suitable number of wires may be employed; three or four such wires are often employed. The wire struts 140 may be sufficiently rigid so as to maintain a desired longitudinal spacing between the stent segments before, during, and after deployment of the stent graft, and may also maintain graft 130 extended to a desired length before, during, and after deployment. The wire struts 140 may be sufficiently flexible so as to enable maneuvering of the stent graft through the vascular system from the introduction site to the repair site. In addition to wire strut(s), any other suitable mechanical configuration and/or material(s) may be employed for forming longitudinal strut(s) 140, including but not limited to configurations and materials disclosed in the above-cited references. The longitudinal struts are shown positioned within the lumen of graft 130, but the stent graft could also be constructed with the longitudinal struts outside the graft 130. The longitudinal struts 140 are shown connected to the outer ends of the stent segments 110 and 120, but may be connected at any suitable point of the stent segments, including the inner end, the outer end, or some intermediate position.

Figure 1B:
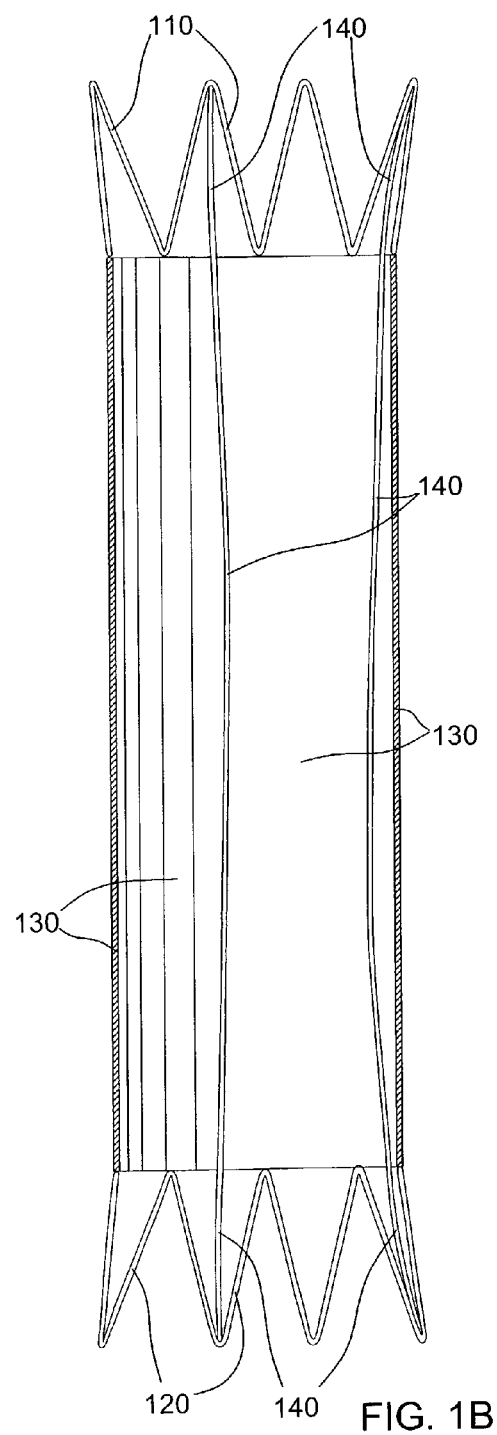

Stent segments 110 and 120 are adapted in any suitable manner for engaging the endoluminal surface of the vessel near the repair site, including but not limited to those disclosed in the above-cited references, in order to establish secure and sable positioning of the stent segments within the vessel. The graft 130 is connected near its outer ends to the stent segments 110 and 120 (directly in FIGS. 1A–1D; to struts 140 in FIGS. 2A–2D), so that engagement of the stent segments serves to anchor the graft within the vessel at the appropriate longitudinal position. In the embodiment of FIGS. 1A–1D, the inner end of each of stent segments 110 and 120 is secured directly to the outer ends of graft 130 by any suitable means, including but no limited to those disclosed in the above-cited references. Stent segments 110 and 120 may therefore serve to form a substantially fluid-tight seal between the ends of graft 130 and the endoluminal surface of the vessel (FIG. 1B). A stent graft configured in this way may be used alone to bridge a damaged section of vessel at the repair site. Alternatively, secondary stent segments 150 (FIG. 1C) and/or stent anastomoses 160 (FIG. 1D; see definition below) may be employed for forming substantially fluid-tight seals between the outer ends of graft 130 and the endoluminal surface of the repaired vessel, instead of relying on stent segments 110 and 120 for this purpose. If needed or desired, secondary stent segments 150 (FIG. 1C) may be deployed within graft 130 to maintain a patent lumen therethrough and/or to provide structural support for the graft and/or the damaged vessel. The secondary stent segments 150 and/or stent anastomoses 160 (whether for sealing, for structural support, or for both) are deployed during subsequent deployment steps after deployment of the initial stent graft, and therefore do not add to the cross sectional size of the stent graft during its deployment.

Figure 15:
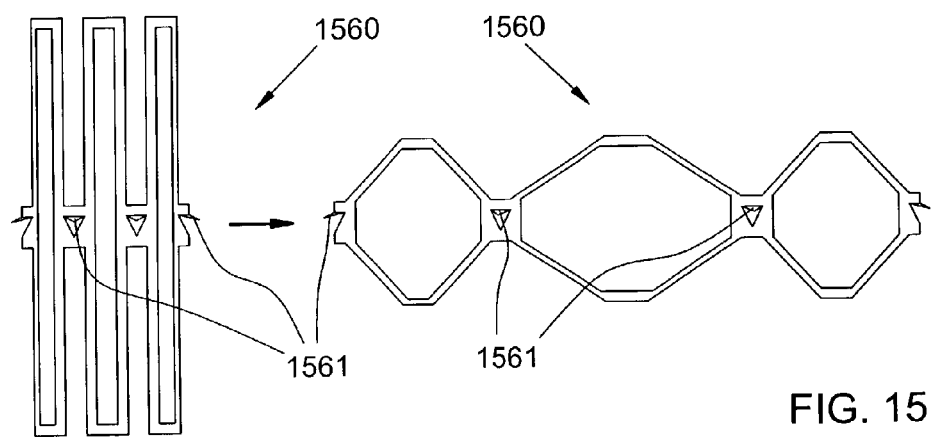
FIGS. 15 and 16 show exemplary embodiments of stent anastomoses.

A stent segment used at an outer end of graft 130 for anchoring the graft to the vessel wall and for forming substantially fluid-tight seals therewith may comprise a so-called stent anastomosis. The term "stent anastomosis" (plural "stent anastomoses") as employed herein shall denote a stent segment having a longitudinal dimension (i.e., length) substantially shorter than its transverse dimension (i.e., diameter) when deployed, so as to serve primarily as an anchor and seal (FIGS. 1D and 2D; FIG. 15). Such a stent anastomosis may also, but not necessarily, serve as structural support for the graft or vessel. The term "stent segment" shall more generally denote stent segments that may serve for positioning, anchoring, sealing, and/or structural support, and may be understood to encompass stent anastomoses as well as stent segments serving primarily as structural support. A stent anastomosis 1560 as shown in FIG. 15 may be adapted for radial expansion in order to compress the graft material against the endoluminal surface of the vessel and thereby form a substantially fluid-tight seal. The shortened longitudinal extent of the stent anastomosis (relative to other ore usual stent segments) minimizes the amount of contact between graft material and stent material, and may therefore reduce wear of the graft material arising from such contact, while nevertheless providing a seal for the graft.

A stent anastomosis as described herein may be further adapted for maintaining the graft in a substantially fixed longitudinal position within the vessel, such adaptation including but not limited to those recited in the above-cited references. In particular, any hook- or barb-type means for fixing the stent anastomosis to the vessel wall may be configured so as to pierce the graft material upon deployment of the stent anastomosis within the graft. The hook or barb passing from the interior of the graft, through the graft material, and into the vessel wall substantially prevents longitudinal movement of the graft material, short of tearing or parting of the graft material. Relying on this piercing of the graft material for securing the graft in a longitudinal position within the vessel, instead of relying on friction between a stent segment, graft, and vessel, may reduce friction-related wear of the graft material.

Figure 16:
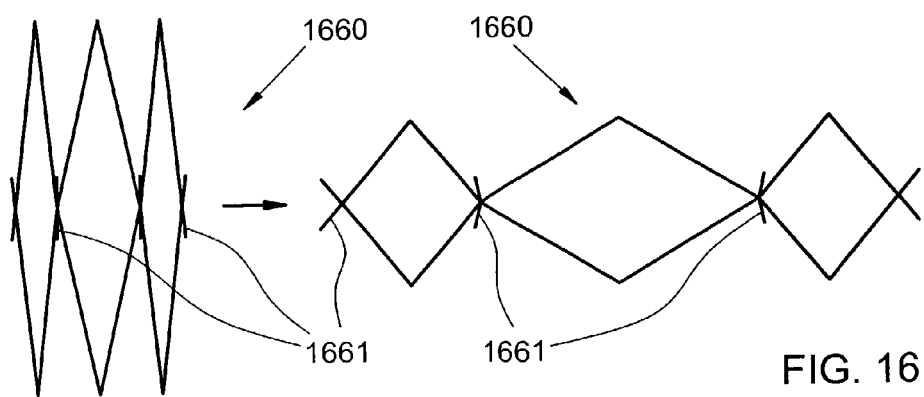

Stent anastomoses (160/260/360/460/560/660) are shown somewhat generically in FIGS. 1D, 2D, 3D, 4D, 5D, 6D, 8, and 9. Exemplary embodiments are shown in FIGS. 15 and 16. In FIG. 15, stent anastomosis 1560 is formed from a tube (nitinol, stainless steel, or other material suitable for forming a stent segment) with cutouts for allowing radial expansion upon deployment. The tube is also cut for forming barbs 1561. Barbs 1561 may be held down by a sheath (part of the deployment hardware; not shown), and allowed to spring into an outwardly protruding position when the sheath is withdrawn from stent anastomosis 1560. The barbs 1561 are pushed through the graft material and into the vessel wall upon radial expansion of stent anastomosis 1560. Such an embodiment may also be formed from wire (not shown). In FIG. 16, barbs 1661 lie nearly flush with the outer surface of a wire stent anastomosis 1660 prior to radial expansion, and then protrude outward upon expansion (for piercing the graft and vessel wall). Paired barbs 1661 are shown in FIG. 16; single barbs could be equivalently employed. An embodiment such as that of FIG. 16 may be fashioned from a tube or from wire. Other embodiments of stent anastomoses not explicitly shown may nevertheless fall within the scope of the present disclosure and/or claims.

Figure 2A:
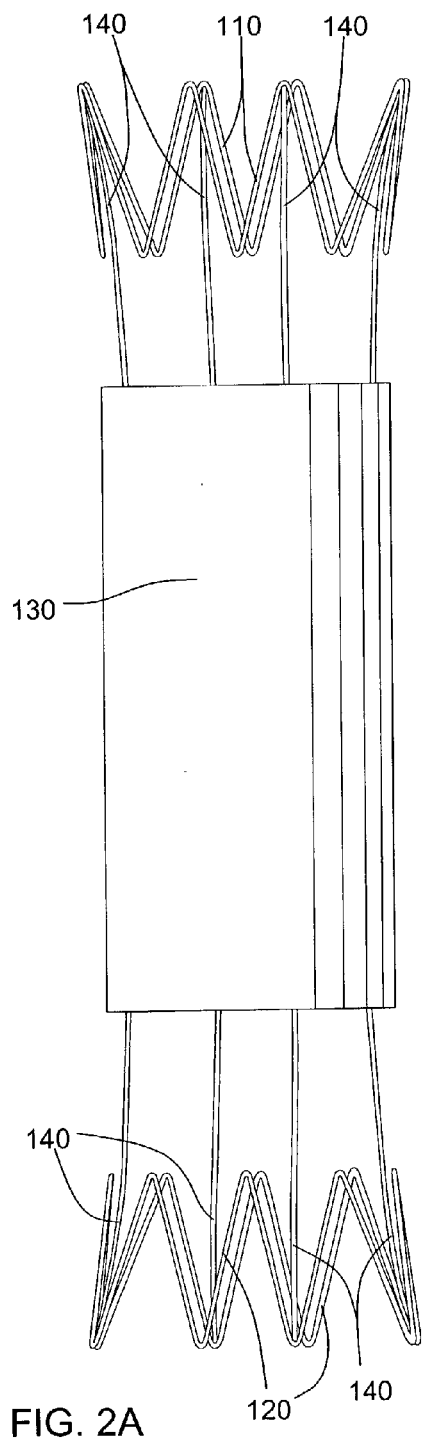
FIGS. 2A–2D show an exemplary embodiment of a stent graft.
Figure 2B:
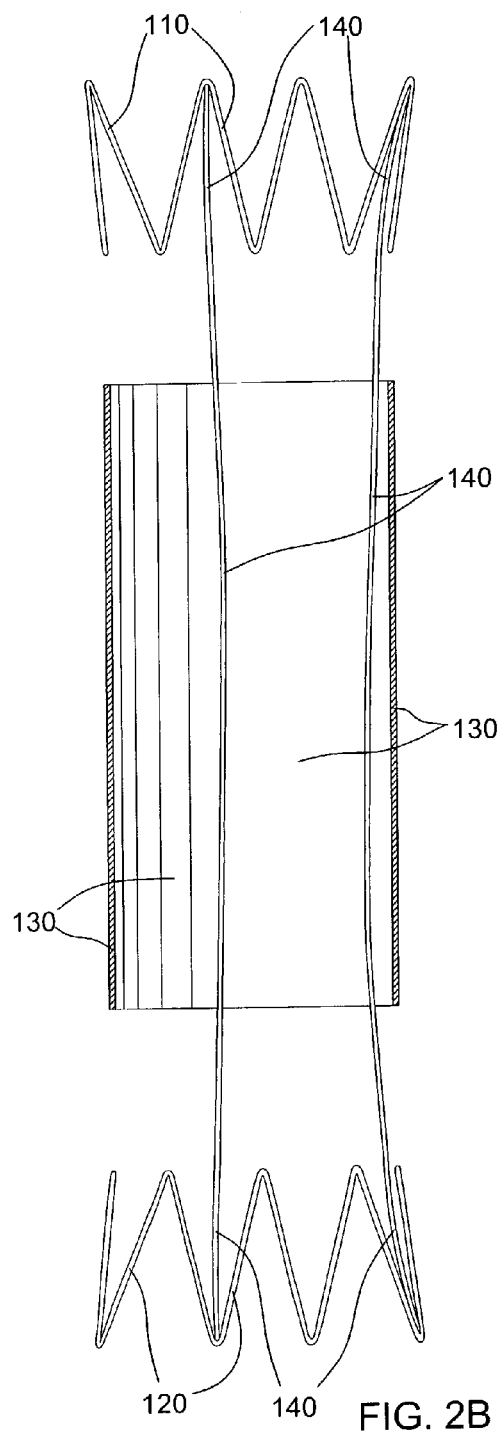
Figures 2C, 2D:
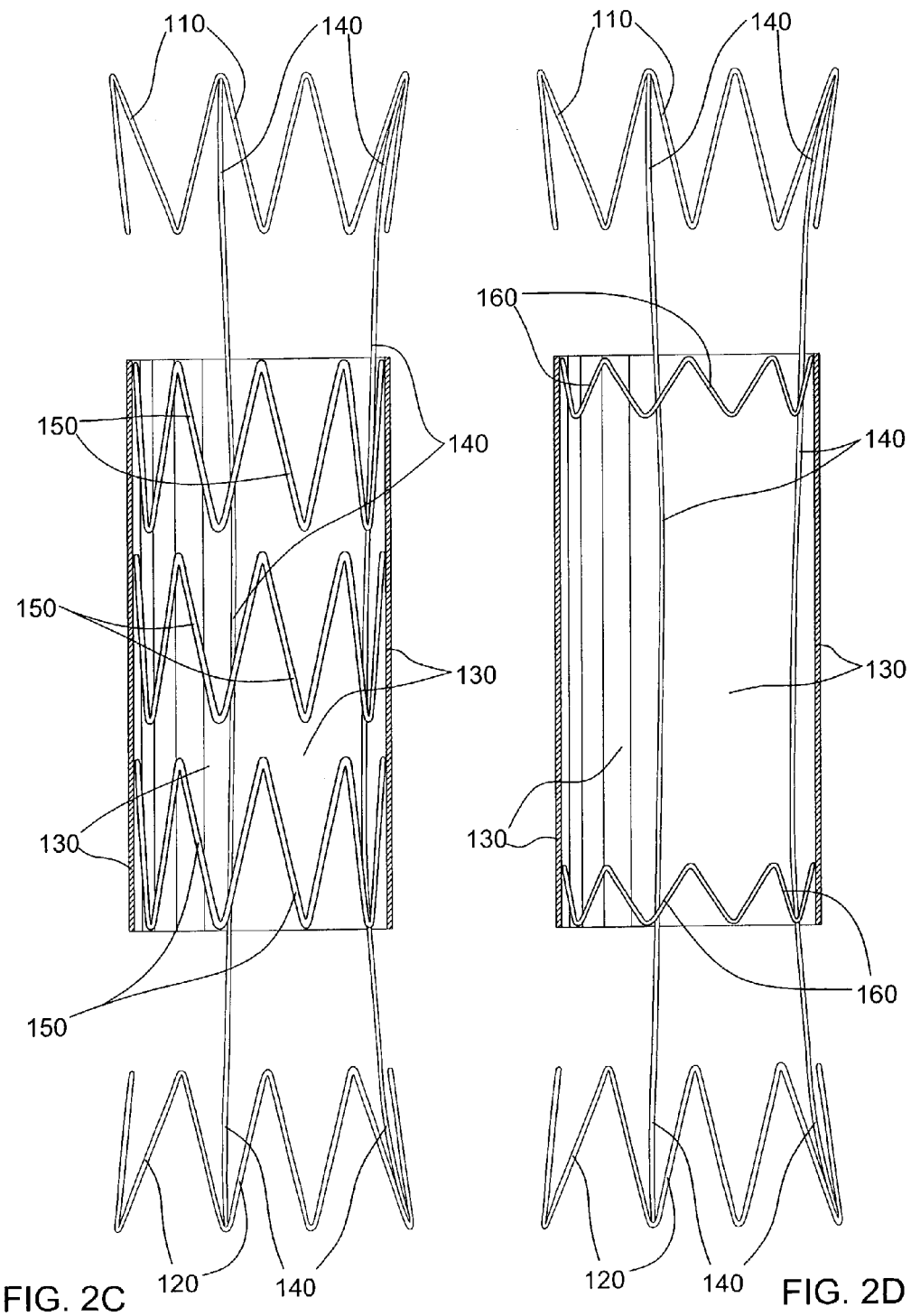

In the embodiment of a stent graft shown in FIGS. 2A–2D, there is a gap between each of the inner ends of stent segments 110 and 120 and the corresponding outer end of graft 130. Such a gap may allow positioning of an end of graft 130 near a vessel branch point while reducing interference of the adjacent stent segment with blood flow through the branch vessel, or may otherwise facilitate positioning of graft 130. Graft 130 is secured to the longitudinal struts 140 in any suitable manner so as to maintain a fixed position relative to the stent segments 110 and 120, so that placement of the stent segments within the vessel may be relied upon for accurate longitudinal positioning of the graft along the vessel at the repair site. In this embodiment, secondary stent segments 150 (FIG. 2C) or stent anastomoses 160 (FIG. 2D) are required at the outer ends of the graft 130 for forming substantially fluid-tight seals between the graft and the endoluminal surface of the vessel. Additional secondary stent segments 150 may be deployed between these outer secondary stent segments if needed or desired for additional structural support (FIG. 2C).

For deployment of the embodiments of FIGS. 1A–1D or 2A–2D, a single introduction site and any suitable deployment hardware (including but not limited to deployment hardware disclosed in the above-cited references) may be utilized for introduction of the stent graft into the intravascular space, maneuvering it to the repair site, and deploying it. The longitudinal strut(s) 140 ensure that as one end of the stent graft is pushed or pulled through the vessel, the spacing between the stent segments 110 and 120 will remain substantially constant, and the graft 130 will remain extended to the desired length. The lack of substantial overlap of the stent segments and the graft enables introduction through a small introduction site and maneuvering through more tortuous vessels. Lack of substantial overlap between stent segments and the graft enables use of thicker, more robust graft material while maintaining small cross sectional size for facilitating introduction and maneuvering of the stent graft. Secondary stent segments 150 and/or stent anastomoses 160 may be introduced, maneuvered, and deployed with any suitable deployment hardware from the same introduction site after deployment of the stent graft, or may be introduced, maneuvered, and deployed from another introduction site if needed or desired. Separate introduction and deployment of secondary stent segments 150 and/or stent anastomoses 160 (as opposed to their incorporation into a single integrated device along with stent segments 110 and 120 and graft 130, as in previous devices) enables a relatively bulky composite stent graft device to be assembled at the repair site from smaller, more readily introduced and maneuvered subcomponents.

Two additional embodiments of a stent graft are shown in FIGS. 3A–3D and 4A–4D. In these embodiments (analogous to the embodiments of FIGS. 1A–1D and 2A–2D, respectively), the longitudinal struts are omitted, thereby further reducing the cross sectional size of the graft portion of the stent graft during introduction and maneuvering through the vessels to the repair site. A first stent segment 210 is secured to a first outer end of graft 230 (either directly as in FIGS. 3A–3D, or through longitudinal links 240 as in FIGS. 4A–4D), while a second stent segment 220 is secured to a second end of the graft 230 (either directly as in FIGS. 3A–3D, or by longitudinal links 240 as in FIGS. 4A–4D). Since there are no rigid struts between the stent segments 210 and 220, they must be positioned and deployed independently. Proper positioning of each of stent segments 210 and 220 serves to extend graft 230 to the desired deployed length (often, but not necessarily, substantially fully extended). Each of stent segments 210 and 220 (and graft 230 secured therebetween) are introduced into the intravascular space at the introduction site and maneuvered to the repair site using any suitable deployment hardware, and deployed to engage the vessel wall. The outer ends of graft 230 are thus secured in their proper longitudinal positions for repairing the vessel. Longitudinal links 240 may be configured in any manner similar or analogous to the longitudinal struts 140 (except of course that they are not connected to both stent segments) and formed from similar material(s).

Figure 3A:
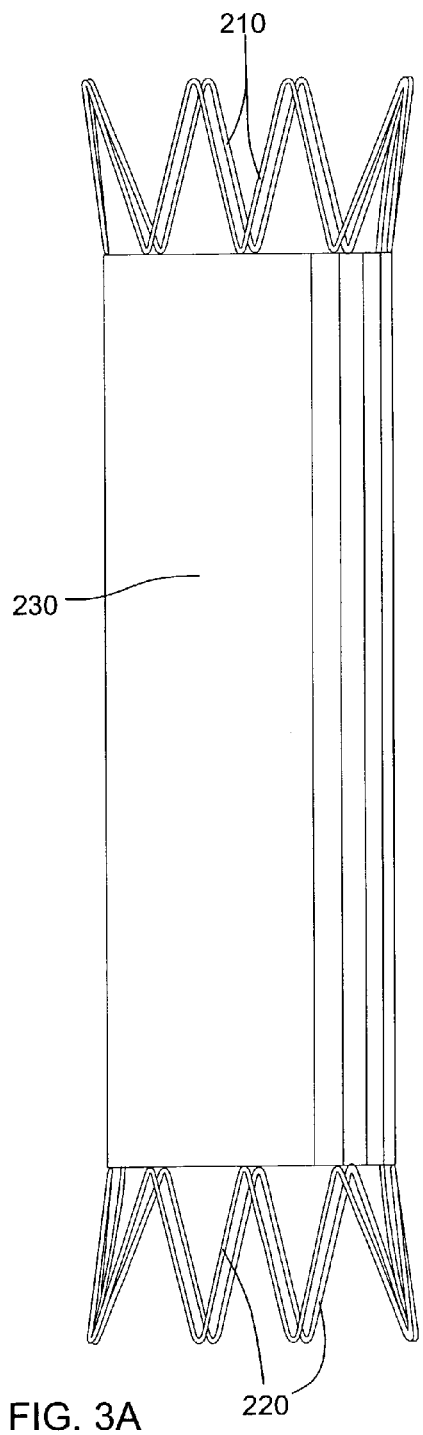
FIGS. 3A–3D show an exemplary embodiment of a stent graft.
Figure 3B:
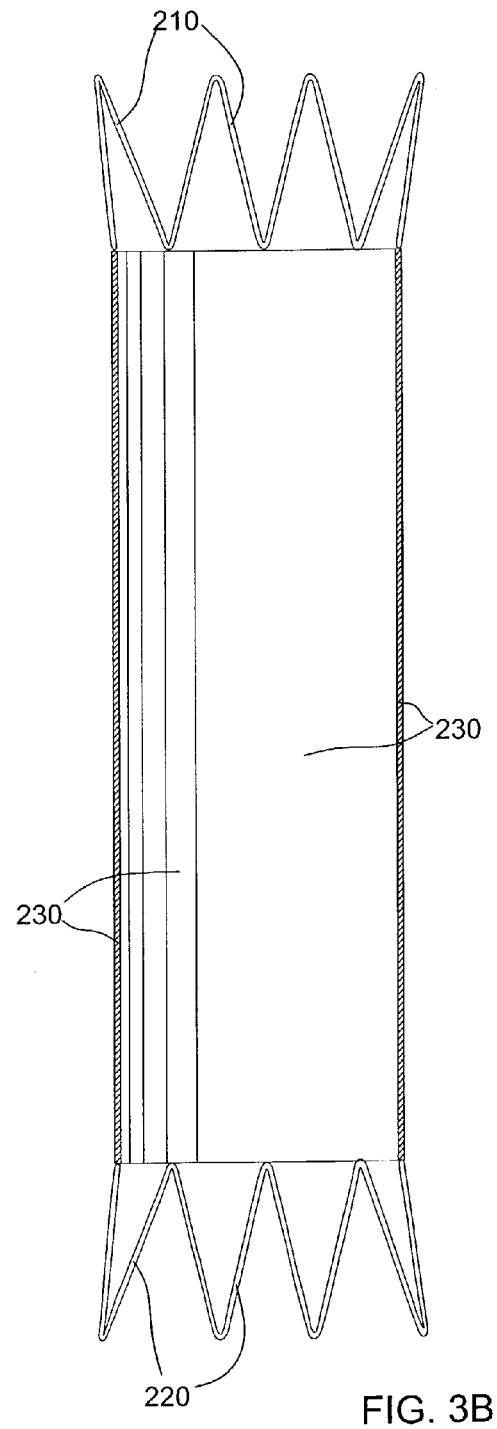
Figures 3C, 3D:
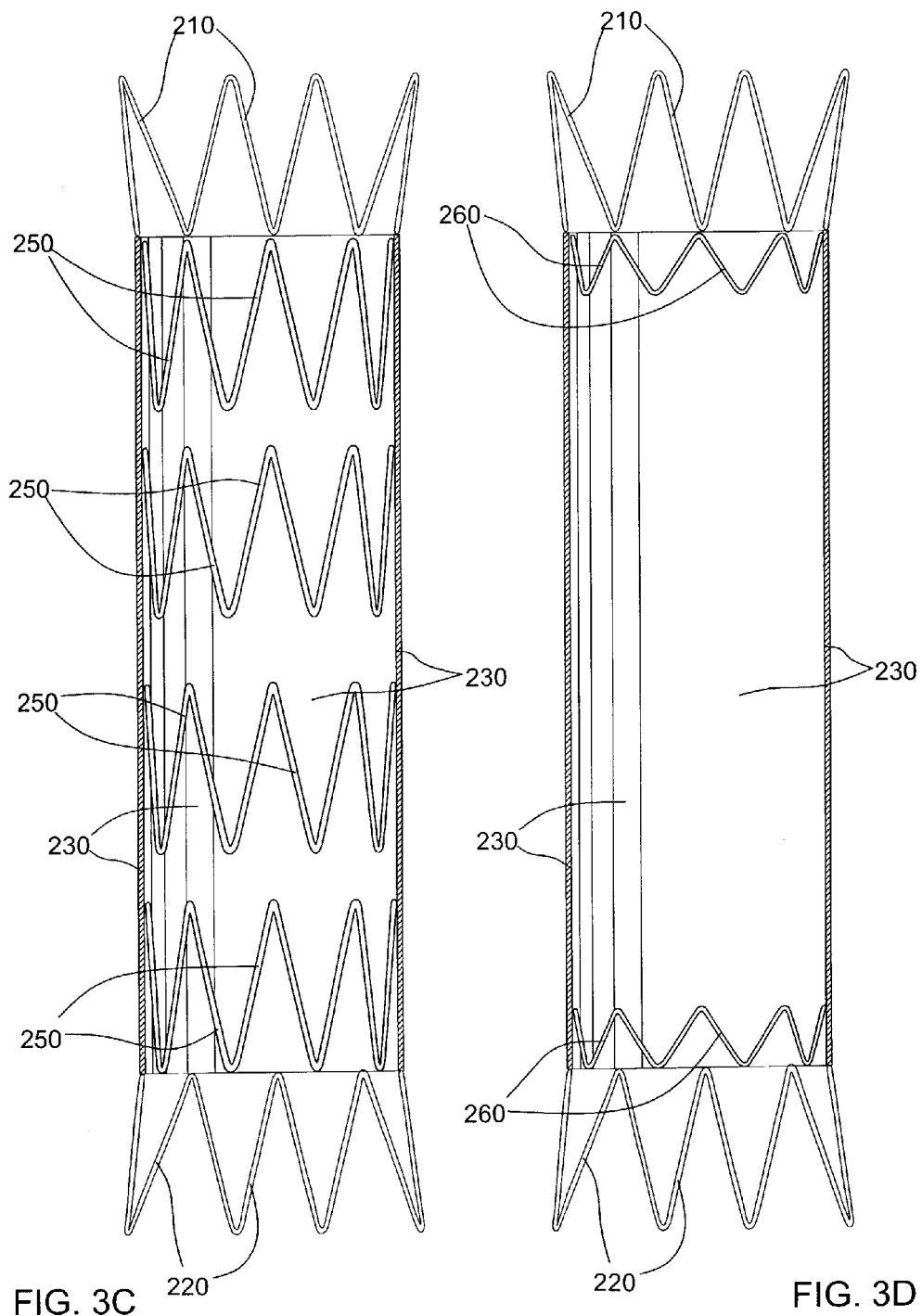
Figure 4A:
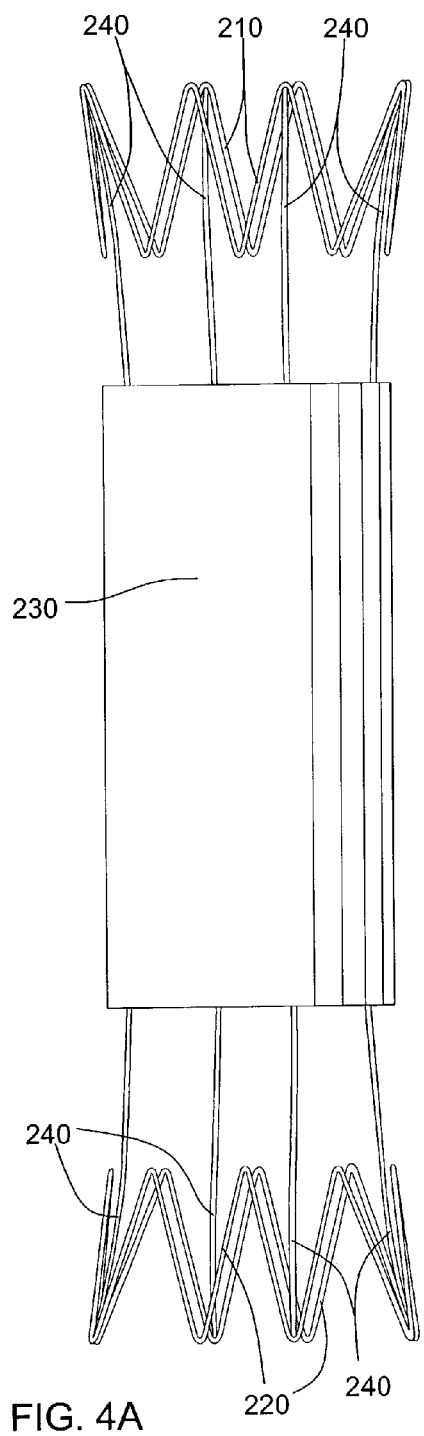
FIGS. 4A–4D show an exemplary embodiment of a stent graft.
Figure 4B:
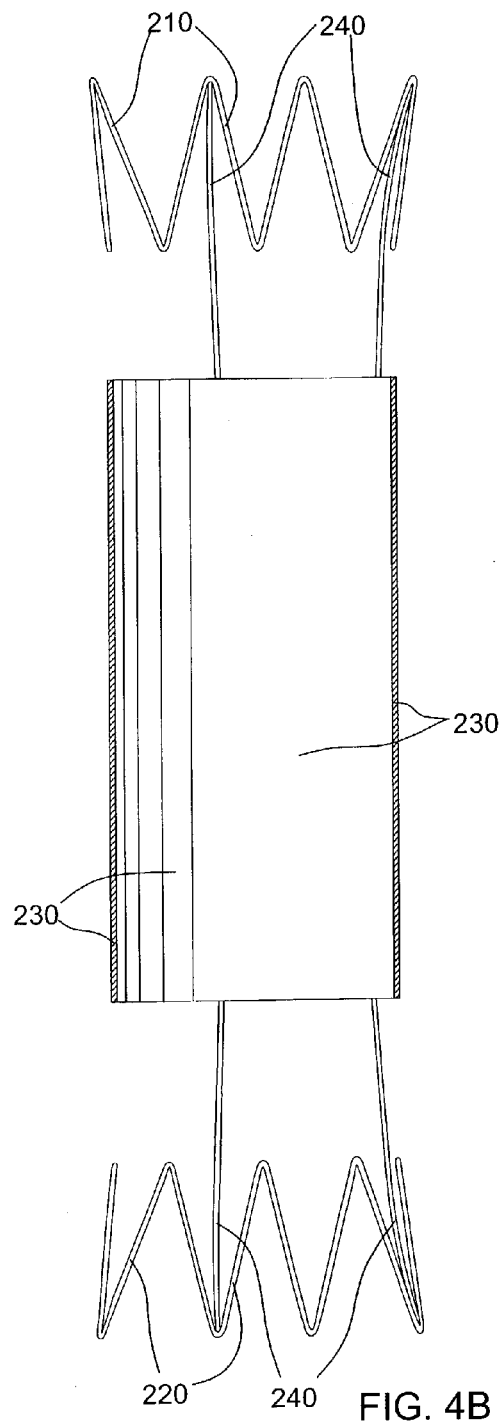
Figures 4C, 4D:
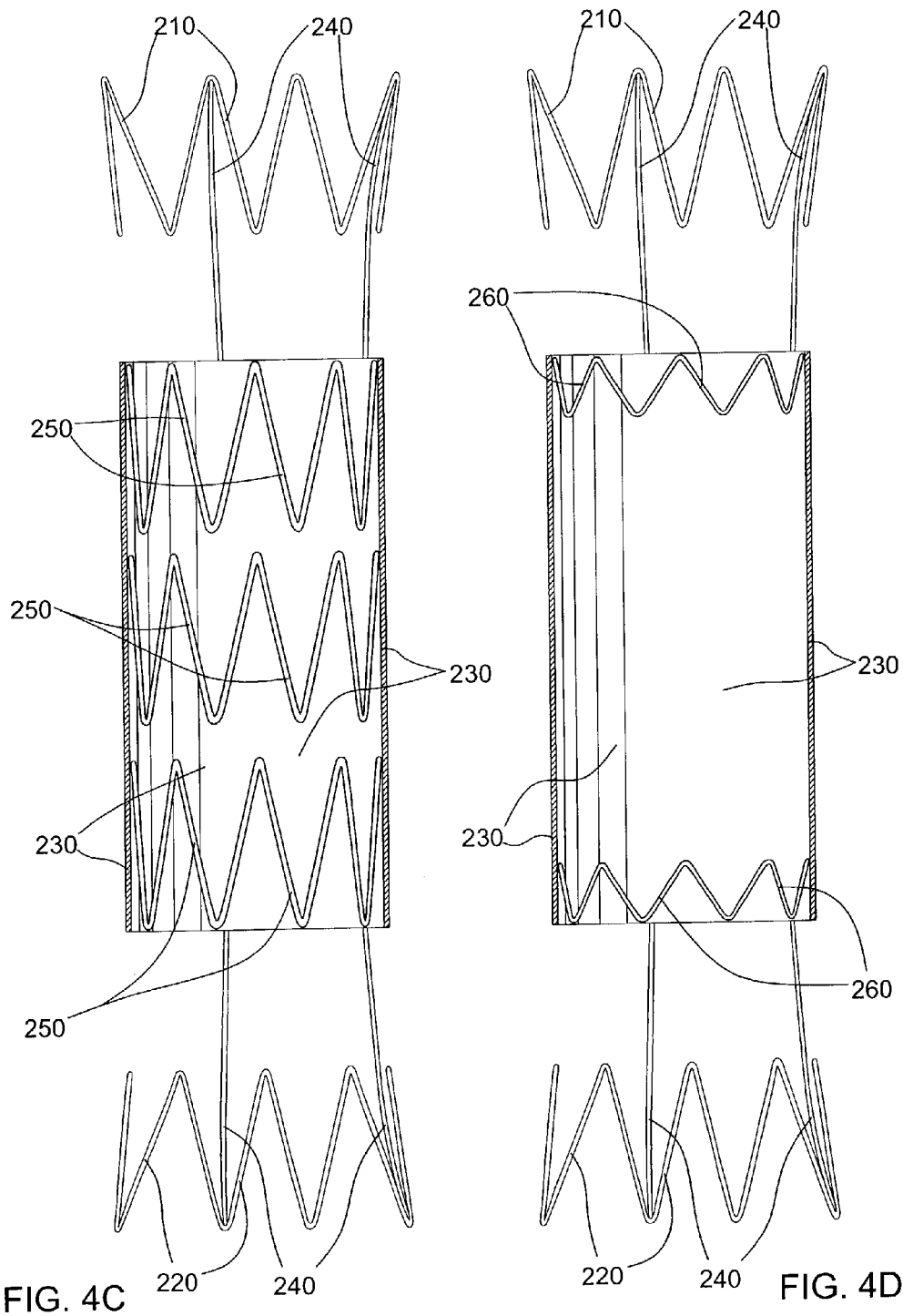

In the embodiment of FIGS. 3A–3D, stent segments 210 and 220 may be adapted to form substantially fluid-tight seals between the outer ends of graft 230 and the vessel wall (FIG. 3B). In this case the stent graft may be employed alone for spanning a damaged section of vessel. Secondary stent segments 250 (FIG. 3C) and/or stent anastomoses 260 (FIG. 3D) may be employed for forming substantially fluid-tight seals between the outer ends of graft 230 and the endoluminal surface of the repaired vessel, instead of relying on stent segments 210 and 220 for this purpose. If needed or desired, secondary stent segments 250 (FIG. 3C) may be deployed within graft 230 to maintain a patent lumen therethrough and/or to provide structural support for the graft and/or the damaged vessel. The secondary stent segments 250 and/or stent anastomoses 260 (whether for sealing, for structural support, or for both) are deployed during subsequent deployment steps after deployment of the initial stent graft, and therefore do not add to the cross sectional size of the stent graft during its deployment.

In the embodiment of a stent graft shown in FIGS. 4A–4D, there is a gap between the inner ends of stent segments 210 and 220 and the outer ends of graft 230. Such a gap may allow positioning of the corresponding end of graft 230 near a vessel branch point while reducing interference of the adjacent stent segment with blood flow through the branch vessel, or may otherwise facilitate positioning of the corresponding end of graft 230. Graft 230 is secured to the longitudinal links 240 so as to maintain a fixed relative position between each outer end of the graft 230 and the inner end of the corresponding stent segment 210 or 220. Placement of the stent segments within the vessel may therefore be relied upon for accurate longitudinal positioning of the outer ends of the graft 230 along the vessel at the repair site. In this embodiment, secondary stent segments 250 (FIG. 4C) or stent anastomoses 260 (FIG. 4D) are required at least at the outer ends of the graft 230, for forming substantially fluid-tight seals between the graft and the endoluminal surface of the vessel. Additional secondary stent segments 250 (FIG. 4C) may be deployed between these outer secondary stent segments if needed or desired for additional structural support.

For deployment of the embodiments of FIGS. 3A–3D and 4A–4D, stent segments 210/220 must be individually positioned at the repair site so as to position graft 230 properly positioned and extended. Various deployment schemes, using any suitable deployment hardware, may be employed for introducing, maneuvering, positioning, and securing the stent graft, including but not limited to the following. (1) The entire device (stent segments 210 and 220 and graft 230) may be introduced and maneuvered within a common sheath or other suitable deployment device to the repair site, followed by individually positioning and securing the stent segments in the desired positions. (2) One stent segment (210 or 220) may be pushed or pulled to the desired position at the repair site (perhaps "dragging" the other stent segment and graft) and secured, using any suitable deployment hardware, and then the other stent segment may be positioned and secured. In this scheme the deployment hardware and the stent graft may be introduced through a single common introduction site, or some of the deployment hardware may be introduced through a second introduction site and used to maneuver position, and/or secure the stent graft. Deployment hardware employed for positioning and/or securing the two stent segments 210 and 220 may be present simultaneously, in side-by-side or concentric arrangement (if introduced from a common introduction site or from the same intravascular direction from different introduction sites) or in an end-to-end arrangement (if introduced from different introduction sites in differing intravascular directions, typically with the stent graft and repair site in between). Alternatively, deployment hardware for positioning and/or securing the first of the stent segments 210 and 220 (often the leading stent segment) may be released from the first stent segment and then used to acquire, position, and secure the second stent segment. Alternatively, deployment hardware for the first stent segment may be released therefrom and removed from the introduction site, and deployment hardware for the second stent segment introduced. This second deployment hardware may be used to acquire, position, and secure the second stent segment. (3) Deployment hardware may be employed at two introduction sites and used to manipulate the stent graft in a push-pull arrangement, thereby facilitating maneuvering and positioning of the stent graft at the repair site. Secondary stent segments 250 and/or stent anastomoses 260 may then be deployed (as needed or desired) from the same introduction site or from another introduction site, using any suitable deployment hardware.

Figure 5A:
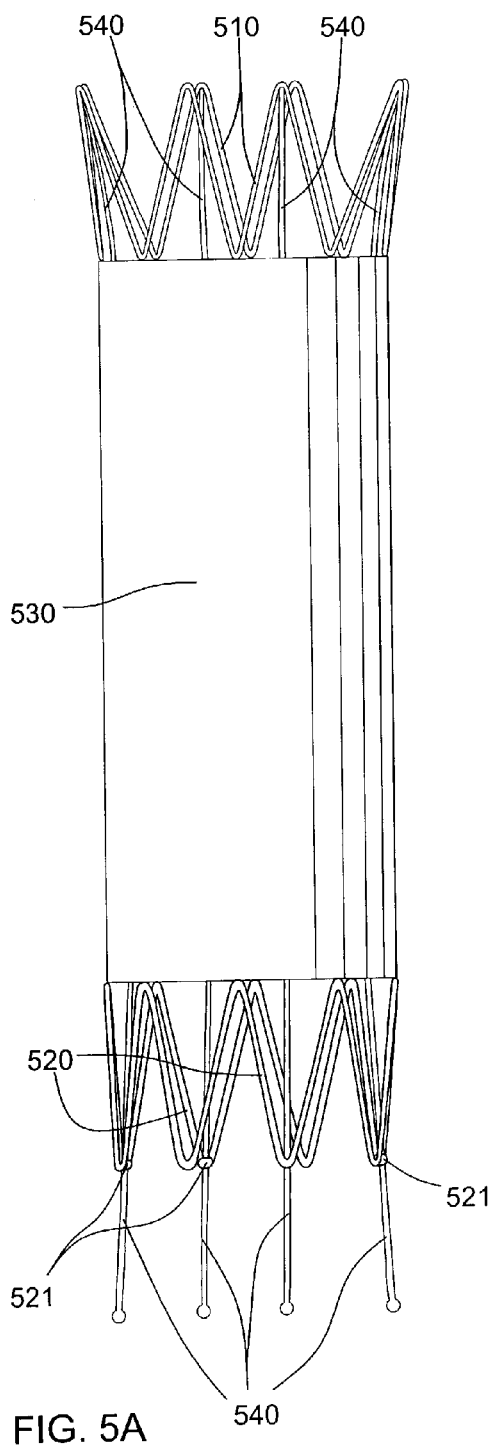
Figure 5B:
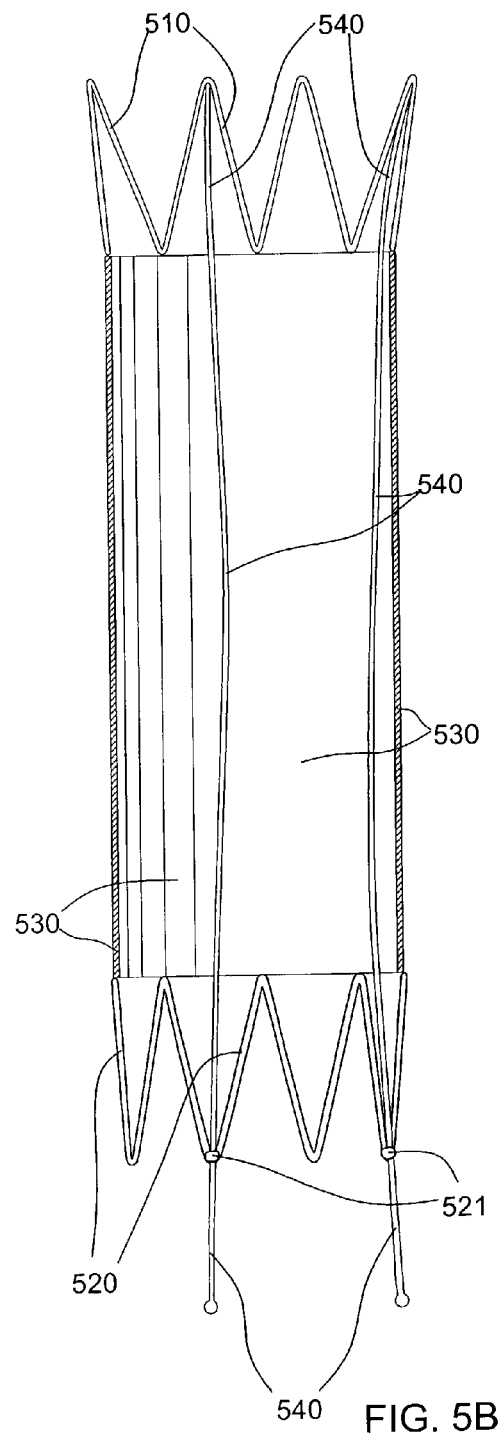
Figure 5C:
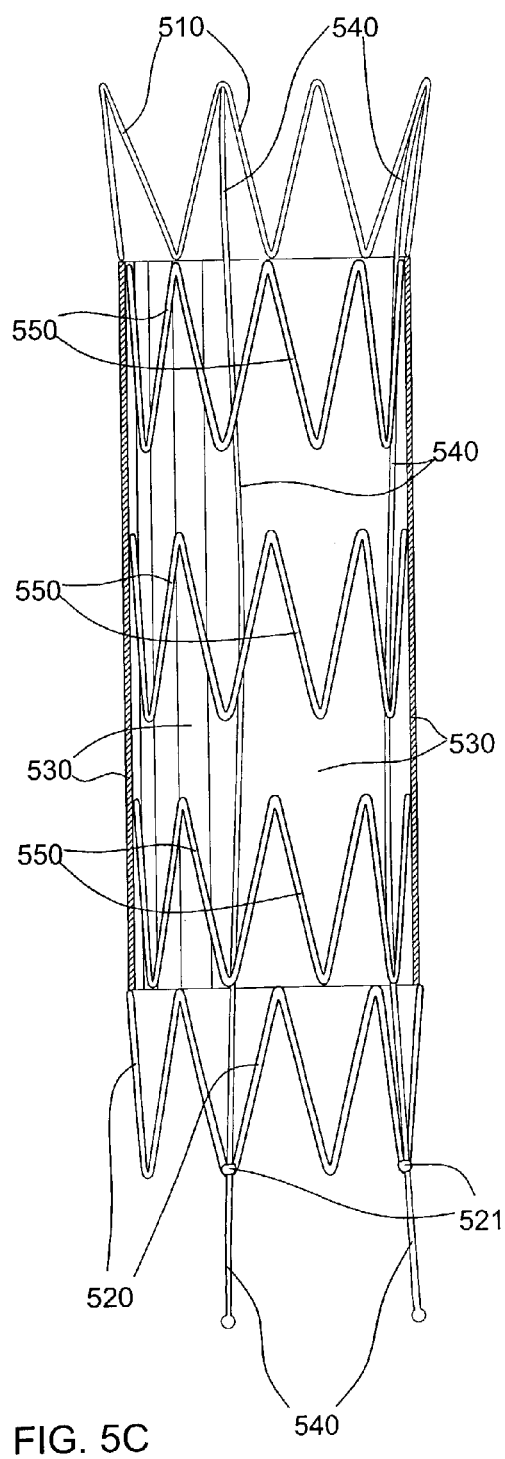
Figure 5D:
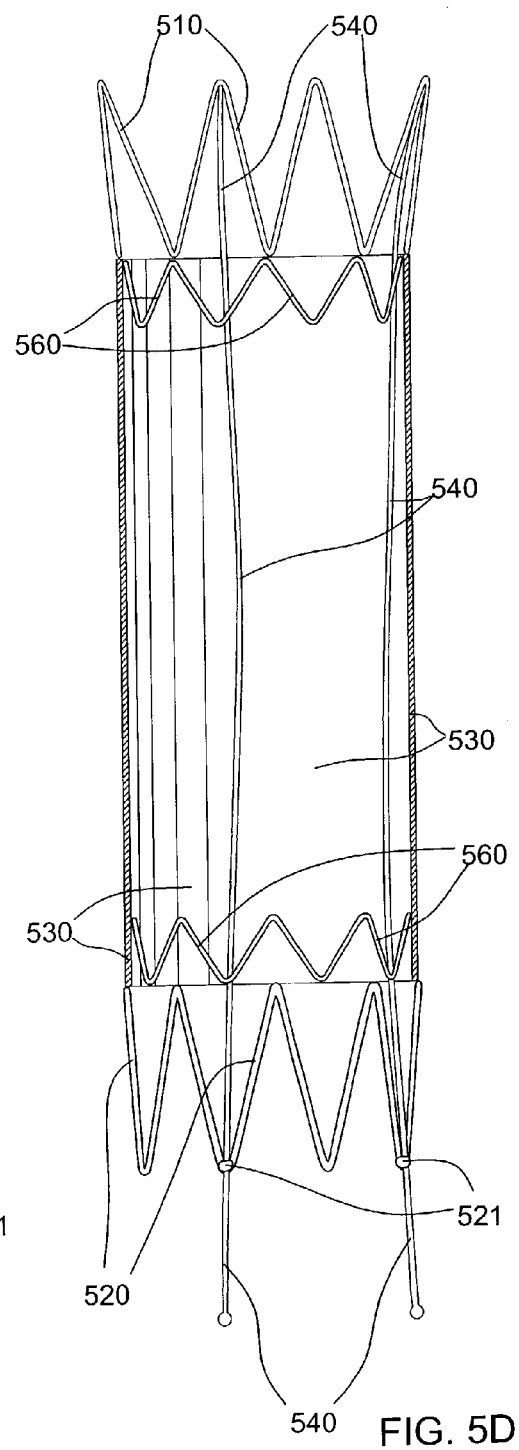
Figure 6C:
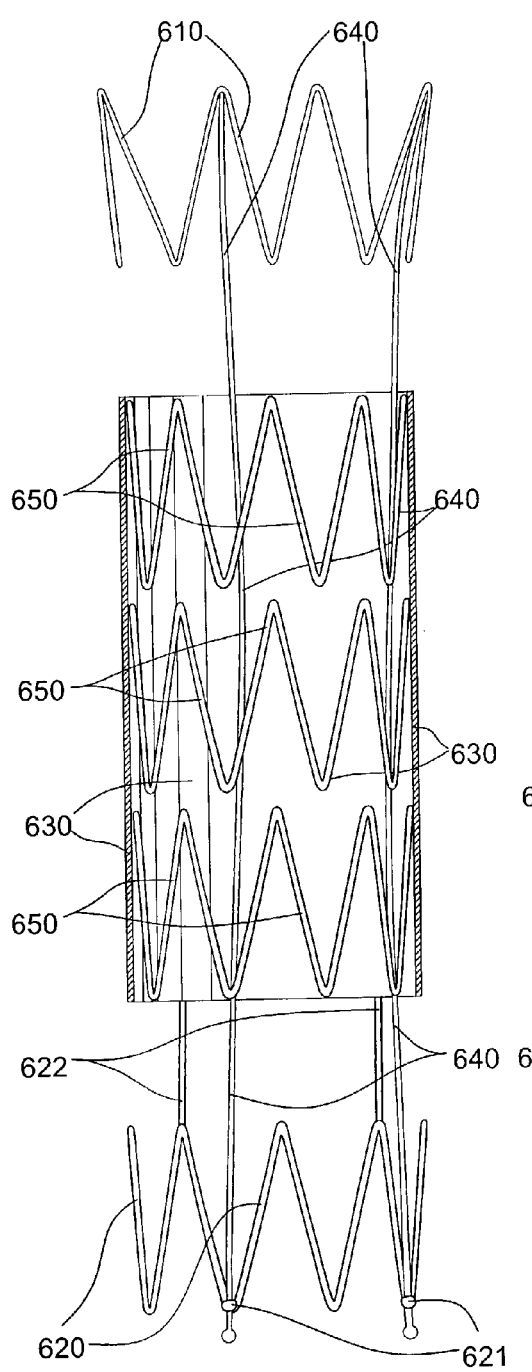
Figure 6D:
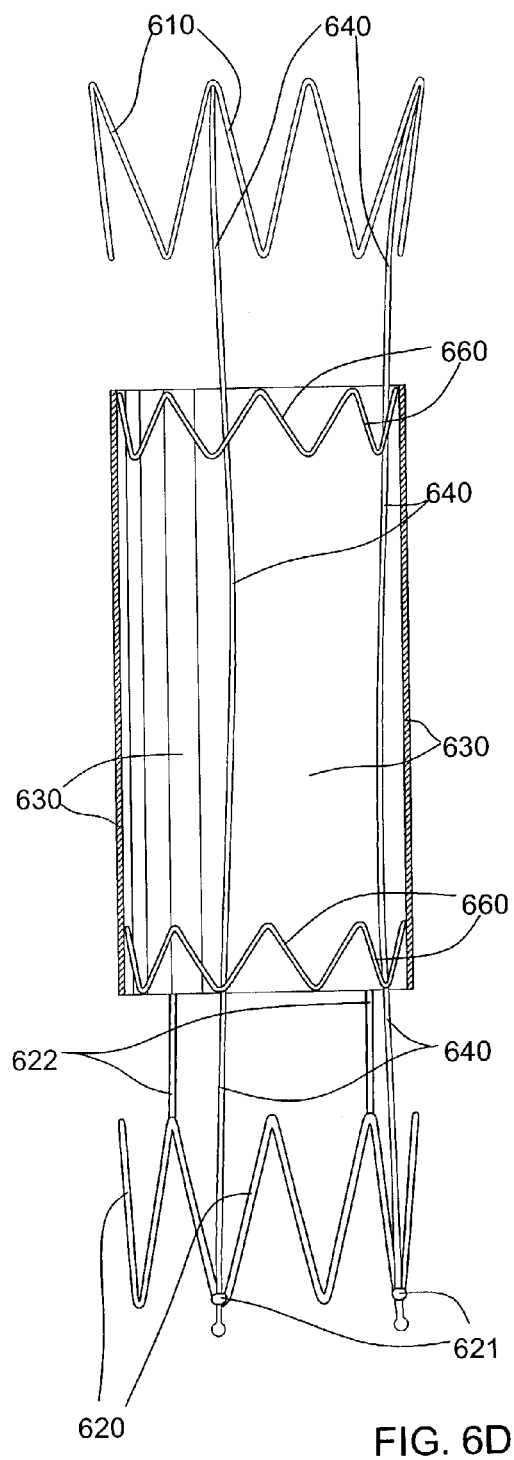
Figure 7A:
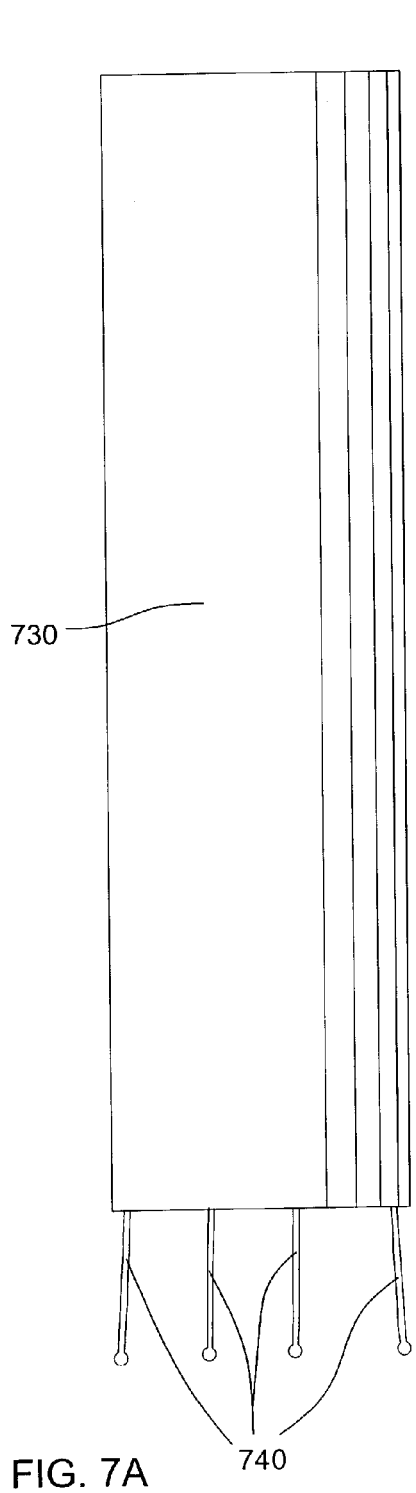
FIGS. 7A–7D show an exemplary embodiment of a stent graft.
Figure 7B:
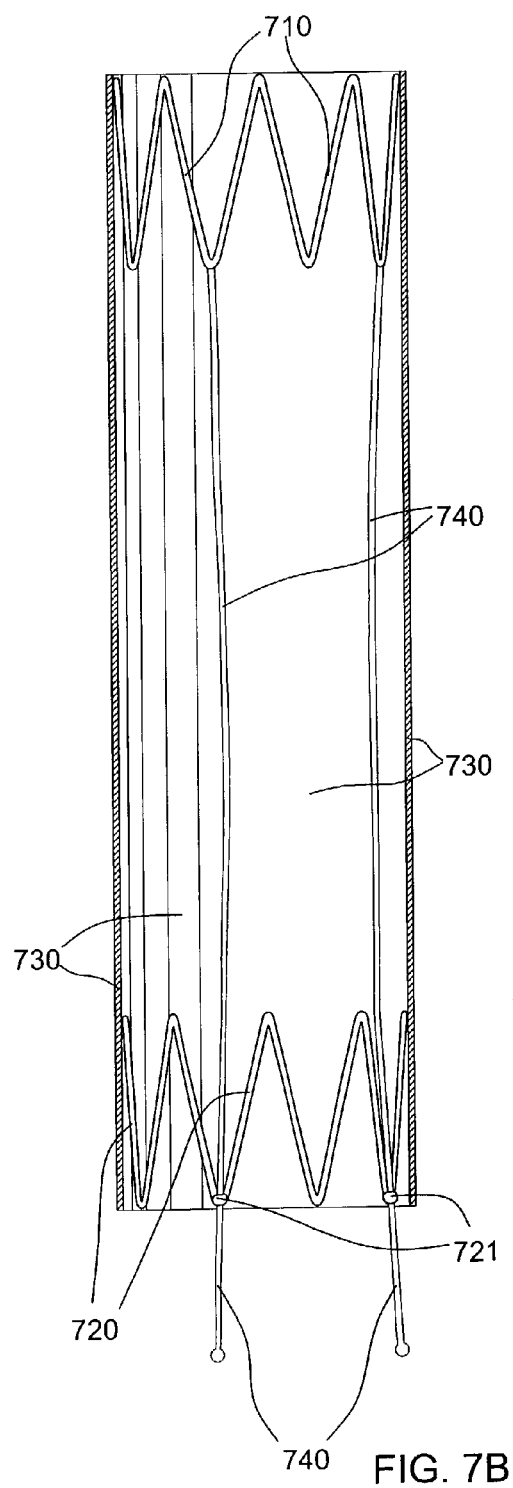
Figures 7C, 7D:
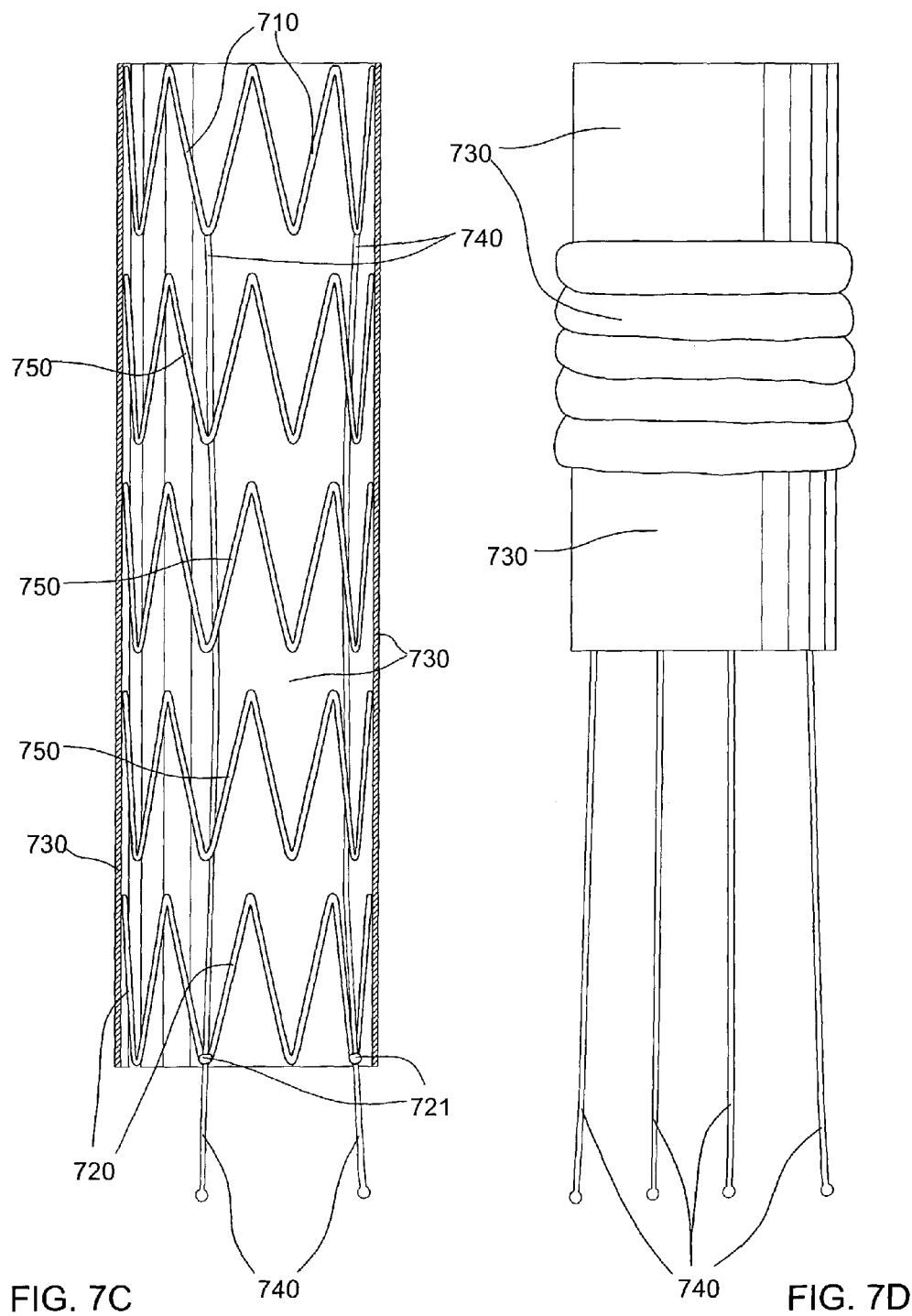

Further variations on the embodiments of FIGS. 1A–1D, 2A–2D, 3A–3D, and 4A–4D are shown in FIGS. 5A–5E and 6A–6E. FIGS. 5A–5E show what might be considered a hybrid embodiment of FIGS. 1A–1D and 3A–3D. Graft 530 is secured at each of its outer ends directly to the inner ends of corresponding stent segments 510 and 520, without substantial overlap of graft 530 and the stent segments. Longitudinal struts 540 are secured at one outer end thereof to stent segment 510 (the "fixed" stent), but are not connected at the other end to stent segment 520 (the "sliding" stent). Instead, longitudinal struts 540 extend through graft 530 and beyond stent segment 520. Stent segment 520 is adapted to slide along longitudinal struts 540 (graft 530 shown substantially fully extended in FIGS. 5A–5D, and compressed in FIG. 5E), with struts 540 passing through loops 521 on stent segment 520. These loops may be formed from wires, sutures, ligatures, or other similar material. The loops 521 are shown on the outer end of Stent segment 520, but could instead be positioned at the inner end, or at an intermediate point on stent segment 520. The sliding engagement of stent segment 520 and the longitudinal struts 540 reduced or substantially eliminates twisting of the graft 530 during maneuvering, positioning, and securing, while facilitating positioning and securing the stent graft in a curved or bent configuration, since each of the longitudinal struts 540 may slide along the stent segment 520 to differing degrees. After engaging stent segment 510 with the vessel walls, stent segment 520 is moved along the longitudinal struts 540 to the desired position and engaged with the vessel walls as well. Stent segments 510 and 520 engage the vessel wall to retain the stent graft in its deployed position at the repair site, and may also serve to from substantially fluid-tight seal between graft 530 and the vessel walls. Secondary stent segments 550 and/or stent anastomoses 560 may be deployed at the ends of graft 530 for forming substantially fluid-tight seals with the vessel walls (FIGS. 5C and 5D), instead of relying on stent segments 510 and 520 for this purpose. Additional secondary stent segments 550 may be deployed along graft 530 for additional structural support, if needed or desired (FIG. 5C).

A similar variation is shown in FIGS. 6A–6E, which may be considered a hybrid between FIGS. 2A–2D and 4A–4D. The embodiment of FIGS. 6A–6E is similar to that of FIGS.

5A–5E, with stent segment 610 connected to longitudinal struts 640, and with sliding engagement between stent segment 620 and the longitudinal struts 640 (through 11 loops 621 on stent segment 620). The outer ends of graft 630 are not connected directly to the inner ends of the stent segments 610 and 620. The outer end of graft 630 closest to stent segment 610 is connected instead to the longitudinal struts 640, leaving a gap between the end of graft 630 and the inner end of stent segment 610. The other end of graft 630 is connected to the inner end of stent segment 620 through longitudinal links 622, leaving a gap between the end of graft 630 and the inner end of stent segment 620. Other than these gaps (possible purposes of which are described hereinabove), deployment and function of the stent graft of FIGS. 6A–6E is analogous to that of FIGS. 5A–5E.

The fixed and sliding stent segment arrangement of FIGS. 5A–5E and 6A–6E may be employed to advantage in more standard stent grafts. The embodiment of FIGS. 7A–7D are similar to those of FIGS. 5A–5E and 6A–6E, except that the graft 730 in this case partly or completely surrounds the stent segments 710 and 720 (as is typically the case with previous stent grafts). However, longitudinal struts are only connected to stent segment 710, while stent segment 720 slides along longitudinal struts 740 (which pass through loops 721 on stent segment 720). Other than this overlap of stent segments and graft (which would increase the cross sectional size of the stent graft during deployment procedures), deployment and function of the stent graft of FIGS. 7A–7D is analogous to that of FIGS. 5A–5E and 6A–6E, with different degrees of sliding along the longitudinal struts facilitating positioning and securing the stent graft at a curved or bent vascular repair site. The stent graft is shown substantially extended in FIGS. 7A–7C, and compressed along struts 740 in FIG. 7D. The stent graft may be used alone to span a vessel segment (as in FIG. 7B). Additional stent segments 750 may be deployed within the stent graft (as in FIG. 7C).

It may be the case in a given clinical situation that once sealing/securing secondary stent segments 150/250 and/or stent anastomoses 160/260 are positioned and secured, stent segments 110/210 and 1201220 may no longer be necessary, having served the function of positioning and securing the graft 130/230 while secondary stent segments were deployed. In some cases the continued presence of stent segments 110/210 and/or 120/220 may even prove to be detrimental, perhaps obstructing or diverting blood flow in undesirable ways. In the embodiments of FIGS. 1A–1E, 2A–2E, 3A–3E, and 4A–4E, stent segments 110/210 and/or 120/220 may be releasably secured to the outer ends of graft 130/230, and may be adapted for enabling disengagement from the vessel walls and withdrawal from the intravascular space. With stent segments 110/210 and/or 120/220 so adapted, they may be released from graft 130/230, disengaged from the vessel walls, and withdrawn from the intravascular space, after secondary stent segments 150/250 and/or stent anastomoses 160/260 are deployed. The stent segments 110/210 and 120/220 serve to move graft 130/230 into place and hold it at the repair site while secondary stent segments 150/250 and/or stent anastomoses 160/260 are deployed, and are then removed when no longer necessary.

Figure 8:
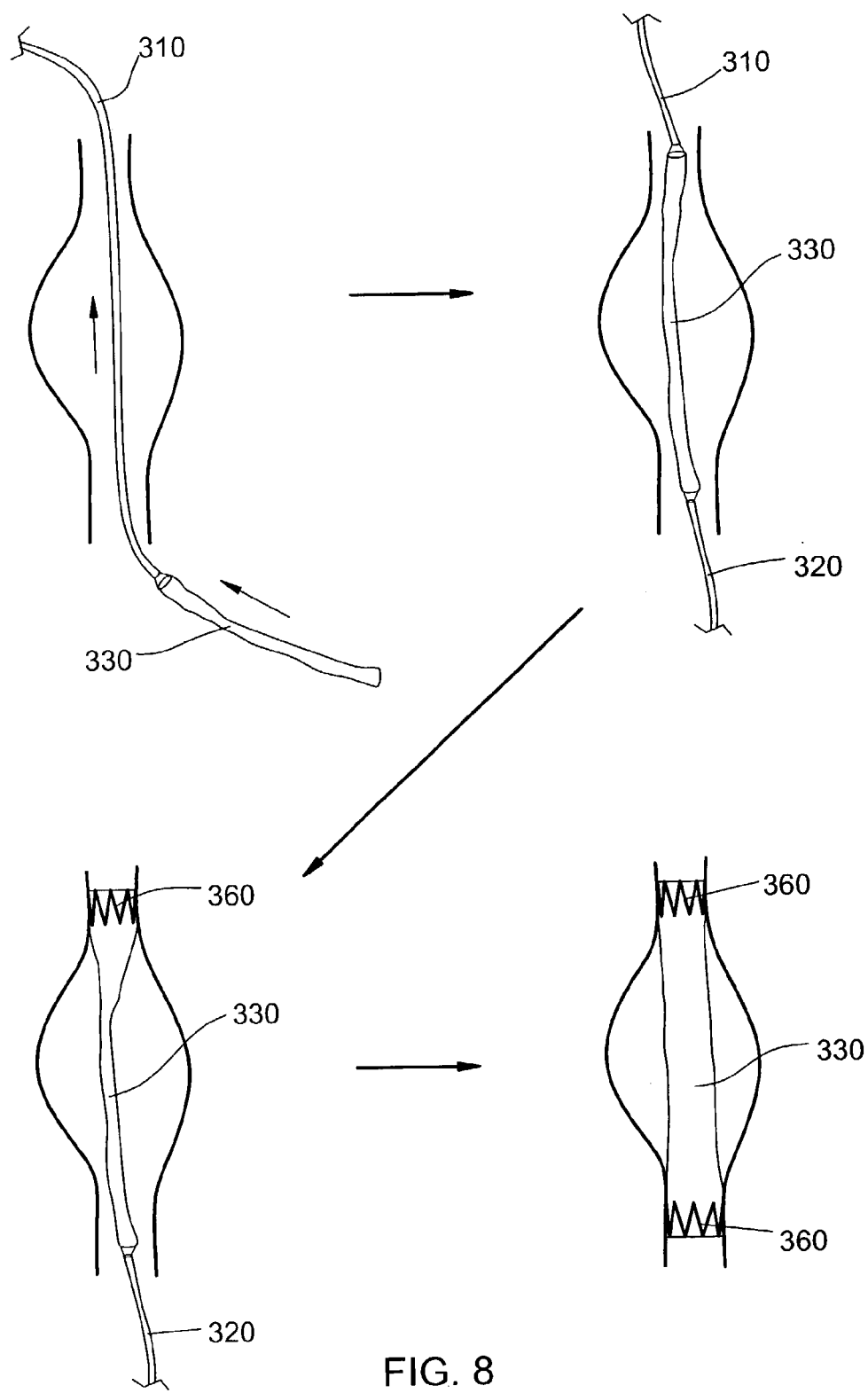
FIG. 8 illustrates a procedure for deploying a stent graft.
Figure 9:
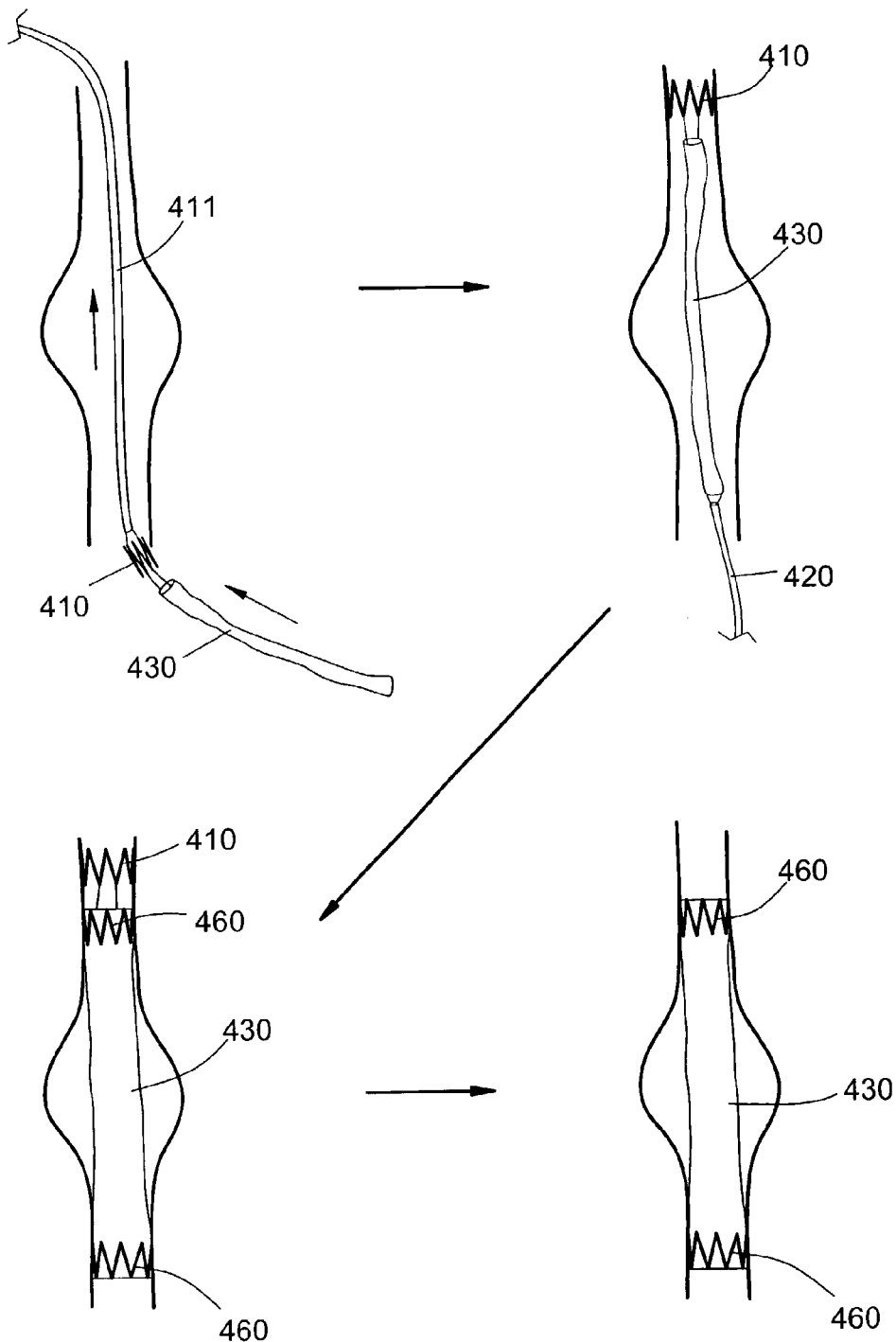
FIG. 9 illustrates a procedure for deploying a stent graft.

Another method for deploying a stent graft enables elimination of stent segments connected to the graft altogether. FIG. 8 illustrates an installation procedure in which the graft 330 is introduced into the intravascular space without any stent segments connected thereto. First and second deployment hardware 310 and 320 are releasably secured to corresponding first and second ends of a graft 330 so that the ends may be maneuvered independently. The first and second deployment hardware 310 and 320 may be introduced into the intravascular pace through corresponding first and second introduction sites, with the repair site in between. The first deployment hardware 310 may be introduced though the first introduction site, maneuvered through the vascular system past the repair site and out through the second introduction site, where it may be releasably secured to the first end of graft 330. The second deployment hardware 320 may be releasably secured to the second outer end of graft 330. The deployment hardware may then be used to maneuver the graft 330 through the intravascular space to the repair site, where the first deployment hardware 310 is used to position the first end of the graft 330. Once the first end of the graft 330 is properly positioned, the second deployment hardware 320 may be employed to properly position the second end of the graft 330 (often, but not necessarily, in an extended configuration). While graft 330 is thus held in place by deployment hardware 310 and 320, additional deployment hardware may be used to deploy stent segments (not shown) or stent anastomoses 360 (shown in FIG. 8) to engage the ends of the graft 330 and the vessel walls, thereby forming substantially fluid-tight seals at the ends of the graft 330 with the vessel walls. Deployment hardware 310 and 320 may then be released from the graft 330 and withdrawn from the intravascular space. Additional stent segments (not shown) may also be deployed within graft 330 between the ends thereof for structural support, if needed or desired.

In a variation of the procedure of the preceding paragraph, the graft 330 may be maneuvered into place with deployment hardware 310 alone, and the first end of the graft 330 secured to the vessel with a stent segment or stent anastomosis. A loop snare or other suitable second deployment hardware 320 may then be introduced and used to acquire the second end of the graft 330 and hold it on place while it is secured to the vessel by a second stent segment or stent anastomosis. In another variation of the procedure of the preceding paragraph, both first and second deployment hardware may be introduced into the intravascular space to approach the repair site from a single common introduction site. In this case the deployment hardware releasably secured to the leading end of the graft 330 would pass through the lumen of graft 330. Secondary stent segments would be deployed around this intra-luminal deployment hardware 310. The deployment hardware 310 and 320 may be in side-by-side or concentric arrangement.

In another variation (FIG. 9) of the preceding procedures, a single stent segment 410 may be employed secured to the leading end of graft 430. Stent segment is maneuvered to the repair site using any suitable deployment hardware (not shown), pulling graft 430 along behind it. Stent segment 410 is engaged with the vessel walls at the repair site so as to properly position the leading edge of the graft 430 and hold it in place during additional deployment steps. A loop snare or other similar deployment hardware 420 is employed to acquire and position the trailing end of graft 430. Alternatively, second deployment hardware may be introduced from the other intravascular direction to pass through graft 430 to extend it and position its second end. However the second end of the graft is positioned, secondary stent segments (sealing 460 and/or structural) are then deployed to secure the graft within the vessel at the repair site. Graft 430 may be left in place, or may be disengaged and withdrawn if releasably connected to graft 430.

Figure 10:
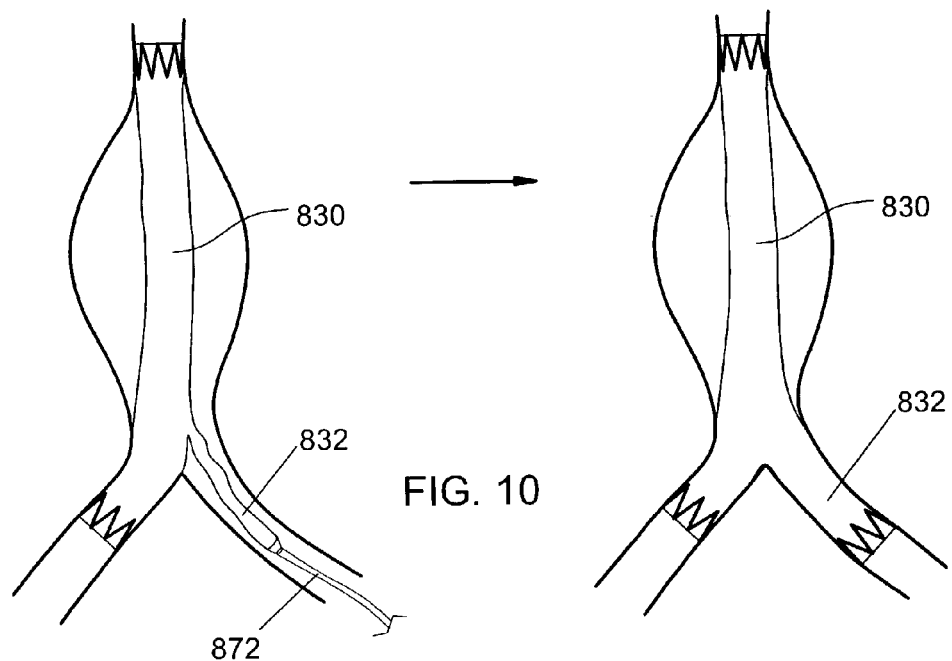
FIG. 10 illustrates a procedure for deploying a stent graft.

In another variation (FIG. 10) of the preceding procedures, a branched graft 830 may be employed having a main channel similar to any of those in the preceding examples (and therefore possibly also including first and/or second stent segments and/or longitudinal struts). Such a stent graft may be suitable for a vascular repair site at, near, or including a vascular branch point. However the main stent graft channel is constructed and deployed, the graft 830 includes a branch channel 832 that has no stent segment or struts. The main stent graft (whatever its form) is deployed by any of the suitable deployment procedure disclosed above. Care is taken during the initial deployment procedure to position the graft branch 832 at the vessel branch point at the repair site. During deployment of the main graft, or perhaps after its deployment, the end of the branch graft 832 is acquired by a loop snare or similar deployment hardware 872, positioned within the vessel branch, and then secured to the vessel with one or more secondary stent segments 870. Alternatively, additional deployment hardware may be used to pass into the branch graft 832 from within the main graft 830 to extend it and position and secure it within the branch vessel.

In typical intravascular deployment procedures, including those disclosed herein, the introduction, maneuvering, positioning, and engagement of intravascular devices such as stent segments and stent grafts are conducted using some sort of imaging technique(s) as a guide. Such imaging may be two-dimensional (such as x-rays or fluoroscopy) or three-dimensional (such as CAT scan or magnetic resonance imaging). Any suitable imaging technique(s) may be employed, including but not limited to those disclosed in the above-cited references. One or more of the stent segments, stent anastomoses, grafts, and deployment hardware may be provided with one or more radiopaque markers for facilitating maneuvering, positioning, and/or engagement thereof within the intravascular space using suitable imaging techniques.

In many previous stent graft deployment procedures, engagement of various stent segments is relied upon for securing the graft in the proper location, and then keeping the graft in place once the deployment procedure is completed. In another class of procedures, one or more suture(s), ligature(s), tether(s), or some analogous deployment/securing hardware or device(s) 910 may be introduced through the vessel wall at the repair site from the extravascular space through an extravascular deployment device 911. A loop snare or other suitable intravascular deployment device 912 is used to acquire the end(s) of ligature(s) 910 and to pull them to an intravascular introduction site, where they are secured to an end of the graft 930. The other end of the ligature(s) 910 may be retained at an extravascular introduction site, labeled, and held for later manipulation of graft 930. The ligatures 910 may be introduced through the extravascular introduction site percutaneously or laparoscopically or by some other suitable procedure using a suitably adapted extravascular deployment device 911. If performed percutaneously, the delivery apparatus (needle, catheter, or similar device) must be guided from the extravascular introduction site to the exterior of the vessel repair site using some sort of imaging technique. Laparoscopic introduction of the ligatures may rely on direct visualization of the exterior vessel wall. Once the repair site has been located (from outside the vessel) a needle or similar device may be employed to pierce the vessel wall and introduce the ligature into the intravascular space. The needle may be acquired along with the ligature 910, pulled through to the intravascular introduction site, removed, and discarded. Multiple ligatures 910 may be introduced through the vessel wall at the repair site circumferentially spaced around the vessel. The graft 930 is pulled into place at the repair site by pulling ligatures 910 through the extravascular introduction site. While thus held in place, stent segments and/or stent anastomoses may be deployed for securing, sealing, and/or supporting graft 930 within the vessel at the repair site. The ligatures may be tied off, clamped, or otherwise provided with a retainer for holding the ligature (and the graft) at the repair site and substantially preventing the ligature from being pulled back into the vessel. A sliding retainer 913 pushed along the ligature against the outside surface of the vessel may serve this purpose.

Figure 11:
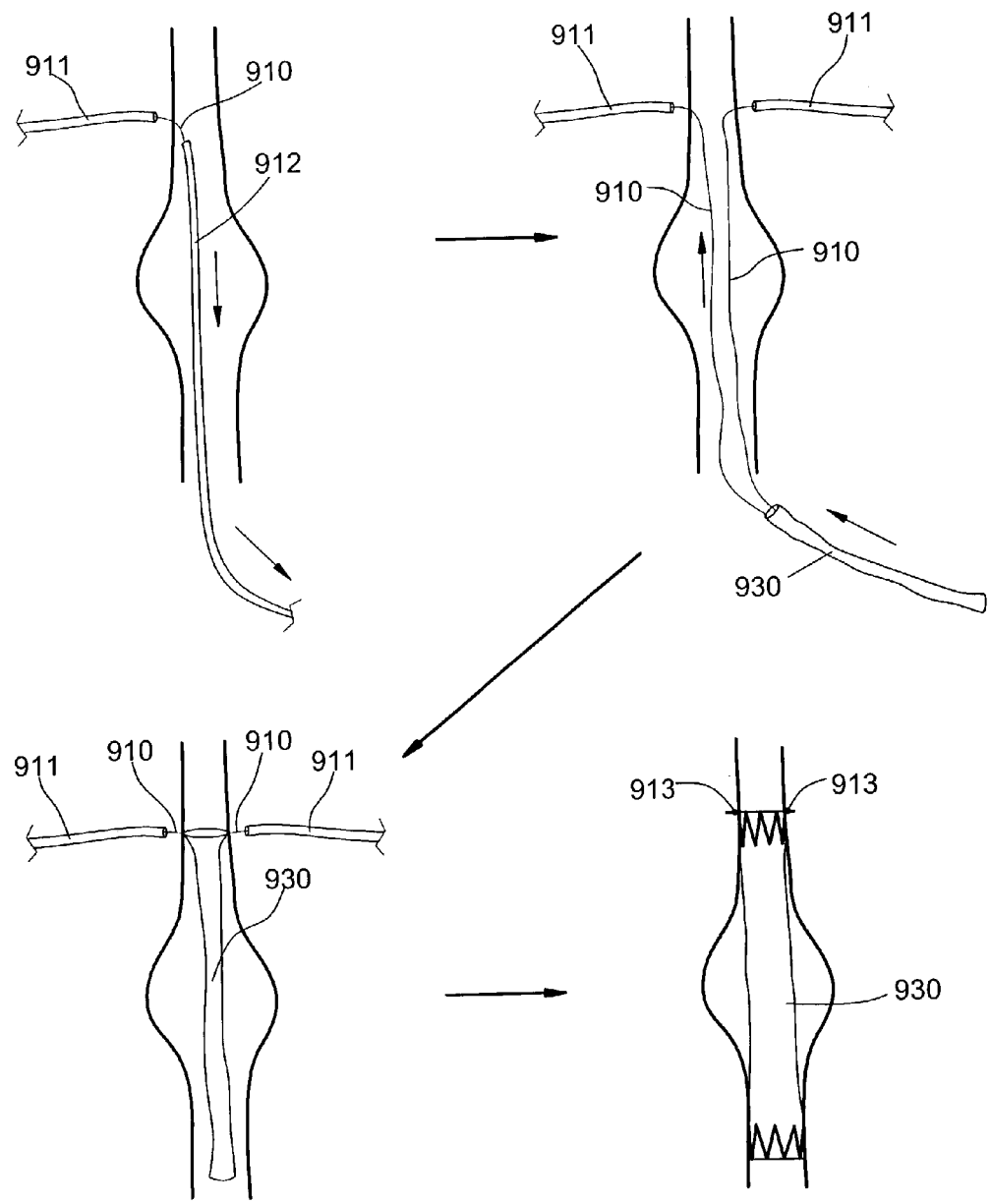
FIG. 11 illustrates a procedure for deploying a stent graft.

Alternatively, the ligature 910 may pass back through the vessel wall and into the extravascular space, thereby forming ligature 910 into a loop within the vessel (not shown). A needle curved or otherwise suitably adapted may be employed to accomplish this. The two ends of the ligature loop may be withdrawn through the extravascular introduction site, labeled, and held for later manipulation of the graft 930. The ligature loop formed within the vessel may be acquired with the intravascular deployment hardware 912 (a loop snare, hook, or similar), pulled through the intravascular space to the intravascular introduction site, and secured to the graft 930 (analogous to FIG. 11). Multiple ligature loops may be introduced through the vessel wall at the repair site circumferentially spaced around the vessel. Once secured to the graft 930, the ligature loop ends are pulled out through the extravascular introduction site to draw graft 930 through the vessels to the repair site (analogous to FIG. 11). With the graft thus held in place, stent segments and/or stent anastomoses may be deployed for securing, sealing, and/or supporting graft 930 within the vessel at the repair site. The ligature loop ends may be tied off, clamped, or otherwise provided with a retainer for holding the ligature (and the graft) at the repair site and substantially preventing the ligature from being pulled back into the vessel. A sliding retainer 913 pushed along the ligature against the outside surface of the vessel may serve this purpose.

In these latter-described deployment procedures, the longitudinal position of the graft end is determined by the point at which the ligatures pierce the vessel wall, and is therefore not subject to slippage or unintended disengagement of a stent segment from the vessel walls. The cross sectional size of the various deployed elements and deployment hardware is also minimal, since no stent segments are employed and the ligatures are typically quite thin.

The trailing end of graft 930 may be positioned and secured in a variety of ways, including any of those described hereinabove. For example, deployment hardware may be introduced through the intravascular introduction site and a loop snare or similar implement used to acquire and position the trailing end of the graft 930, which may then be secured to the vessel wall with a stent segment or stent anastomosis deployed using any suitable method and deployment hardware. Alternatively, a second intravascular introduction site may be employed, and deployment hardware passed therethrough and through graft 930 to acquire and position the trailing end of graft 930 and secure it the vessel wall with a stent segment or stent anastomosis.

Figure 12:
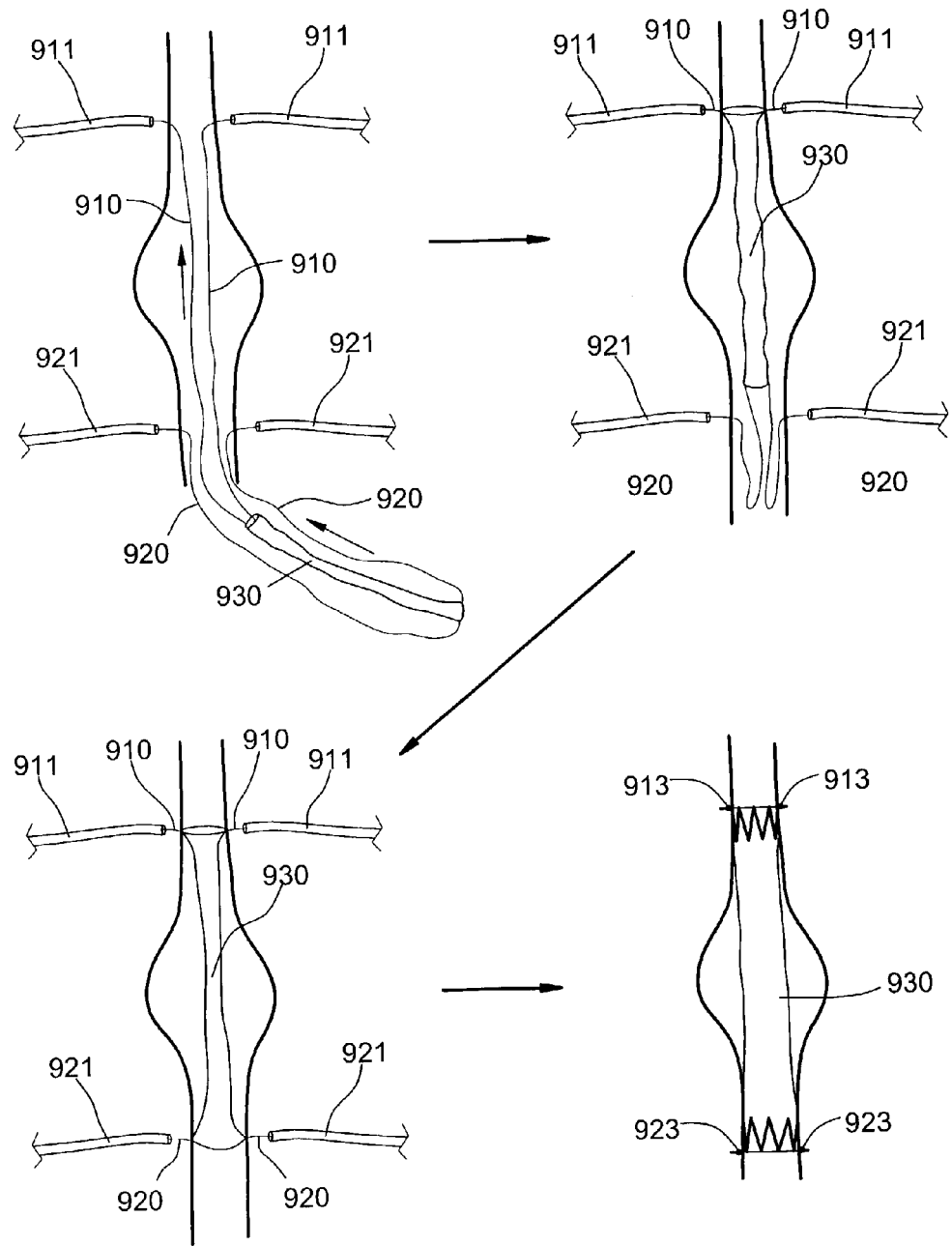
FIG. 12 illustrates a procedure for deploying a stent graft.

In a another deployment procedure, before graft 930 is inserted into the vessels, a second set of ligatures or ligature loops 920 may be introduced through the vessel wall at a repair site position displaced longitudinally from the position of the first ligatures (so that the two ligature positions bracket the repair site; FIG. 12). This second set of ligatures 920 may be pulled through the vessels and out of the intravascular introduction site (through extravascular deployment hardware 921) in a manner similar to the first set of ligatures 910. The second set of ligatures may be secured to the trailing end of the graft 930. Once the leading edge of the graft 930 is secured with ligatures 910 (as described hereinabove), the second set of ligatures 920 may be pulled out through the extravascular introduction site until the trailing end of the graft 930 is pulled tight against the vessel wall, and then tied off or otherwise retained outside the vessel, as described hereinabove (with retainers 913/923, for example). Longitudinal positioning of the trailing end of graft 930 is determined by the point at which the second set of ligatures 920 pierces the vessel wall, and is therefore not subject to slippage or unintended disengagement of a stent segment from the vessel wall. The positions of the first and second ligature sets along the vessel are chosen to provide the desired degree of extension of the graft 930 when the ligatures are pulled snug and tied off or otherwise retained. Substantially fluid-tight seals may be formed at the ends of graft 930 that are secured with ligature loops using stent segments or stent anastomoses. Such stent segments and/or stent anastomoses are not relied upon for maintaining the longitudinal position of the graft, and may therefore be smaller and/or lighter and accordingly more readily maneuvered and positioned at the repair site.

A graft 930 secured at one or both ends with ligature(s) and/or ligature loop(s) may be provided with additional secondary stent segments for providing structural support, in addition to stent segments or stent anastomoses provided for forming substantially fluid-tight seals with the vessel wall.

Figure 13A:
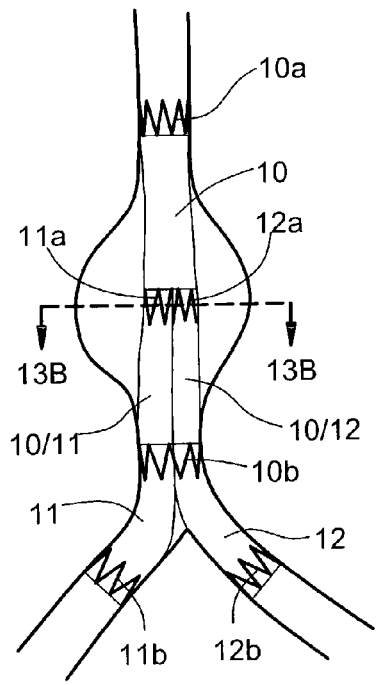
FIGS. 13A–13B show an exemplary embodiment of a branched stent graft.
Figure 13B:
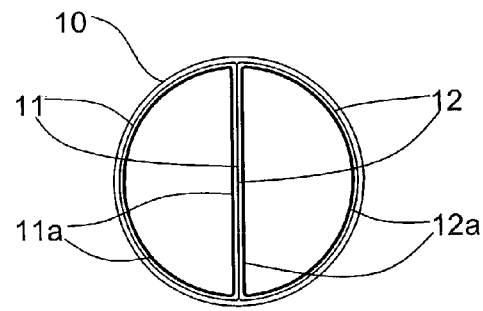

Once deployed and secured at a vessel repair site, any of the embodiments disclosed herein may serve to facilitate deployment of so-called twin-tube stent grafts at bifurcated vessel repair sites, as shown in FIGS. 13A–13B. After a main stent graft is deployed and secured (including graft 10 and stent segments 10*a* and 10*b*), twin-tube branch stent grafts may be introduced, maneuvered to the repair site and into the main stent graft. Respective stent segments 11*a* and 12*a* at the proximal ends of the branch stent grafts are engaged side-by-side within the main stent graft. Stent segments 11*a* and 12*a* are each at least partly covered by a proximal portion of respective grafts 11 and 12, and are adapted so that when engaged side-by-side within the main stent graft, each forms a "D"-shape, with the stent segments 11*a* and 12*a* (and the corresponding 11 graft material covering them) meet and form a septum across the lumen of the main stent graft (FIG. 13B). Gianturco Z-type stents are known to assume such a shape and substantially seal the entire main graft channel upon side-by-side deployment, and may be employed as stent segments 11*a* and 12*a*. Any other suitable stent type that serves to similarly substantially fill and substantially seal the entire main graft channel may be equivalently employed. Once the proximal ends of the branch stent grafts are engaged with the interior surface of main graft 10, the distal ends of the branch stent grafts (each including corresponding stent segments 11*b* and 12*b*) may be engaged with the vessel walls of the corresponding branch vessel. Any suitable graft configuration(s) and/or material(s) may be used for grafts 11 and 12, while any suitable stent configuration(s) and/or material(s) may be used for stent segments 11*b* and 12*b*. Additional secondary stent segments (not shown) may be deployed within the branch stent grafts if needed or desired for forming substantially fluid-tight seals and/or for providing structural support.

Figure 14A:
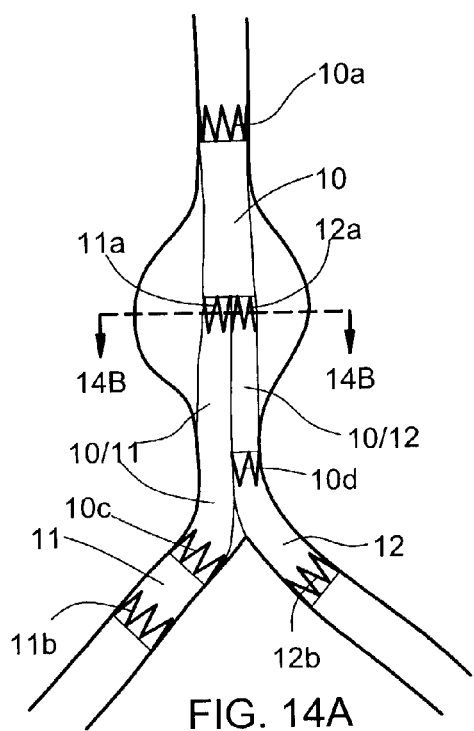
FIGS. 14A–14B show an exemplary embodiment of a branched stent graft.
Figure 14B:
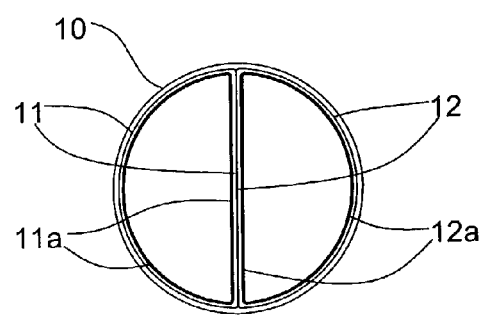

Instead of deploying twin-tube stent branch within a main stent graft having a single lumen, twin-tube stent grafts may be deployed engaged within branched stent grafts such as those disclosed in U.S. Pat. No. 6,319,278, incorporated by reference hereinabove. FIGS. 14A–14B show a bifurcated stent graft, including graft 10 and stent segments 10*a*, 10*c*, and 10*d*. After the bifurcated stent graft is deployed and secured (in the main vessel and perhaps also in one or both branch vessels), twin-tube branch stent grafts are deployed and engaged side-by-side within the main channel of the bifurcated stent graft. Each of the branch stent grafts (which include respective grafts 11/12, proximal stent segments 11*a*/12*a*, and distal stent segments 11*b*/12*b*) passes out through one of the branch channels of the bifurcated stent graft. Proximal stent segments 11*a* and 12*a* are engaged side-by-side within the main channel of the bifurcated stent graft. Stent segments 11*a* and 12*a* are each at least partly covered by a proximal portion of respective grafts 11 and 12, and are adapted so that when engaged side-by-side within the main channel of the bifurcated stent graft, each forms a "D"-shape, with the stent segments 11*a* and 12*a* (and the corresponding graft material covering them) meet and form a septum across the lumen of the main channel of the bifurcated stent graft (FIG. 14B). Stent segments 11*a* and 12*a* may comprise any suitable stent type that serves to substantially fill and substantially seal the entire main graft channel when thus deployed side by side. Once the proximal ends of the branch stent grafts are engaged with the interior surface of the main channel of the bifurcated stent graft, the distal ends of the branch stent grafts (each including a corresponding stent segment 11*b* or 12*b*) may be engaged with the vessel walls of the corresponding branch vessel. Any suitable graft configuration(s) and/or material(s) may be used for grafts 11 and 12, while any suitable stent configuration(s) and/or material(s) may be used for stent segments 11*b* and 12*b*. Additional stent segments (not shown) may be deployed within the branch stent grafts, if needed or desired, for forming substantially fluid-tight seals and/or for providing structural support within the branch channels of the bifurcated stent graft. Additional secondary stent segments (not shown) at other positions may be deployed within the branch stent grafts if needed or desired for forming substantially fluid-tight seals and/or for providing structural support.

It is intended that modifications to the disclosed embodiments may be made without departing from inventive concepts disclosed and/or claimed herein.

What is claimed is:

1. A method for deploying an intravascular stent graft at an intravascular repair site, comprising:

inserting the graft into an intravascular space through an introduction site, the introduction site being remote from the repair site;

maneuvering the graft through the intravascular space to the repair site;

positioning a first end of the graft at the repair site;

inserting a first sealing stent segment, independently of the graft, into the intravascular space though an introduction site, the introduction site being remote from the repair site;

maneuvering the first sealing stent segment, independently of the graft, through the intravascular space to the repair site;

securing the first end of the graft within a vessel at the repair site;

engaging the first sealing stent segment with the first end of the graft, thereby forming a substantially fluid-tight seal between the first end of the graft and an endoluminal surface of the vessel at the repair site;

positioning a second end of the graft at the repair site;

inserting a second sealing stent segment, independently of the graft, into the intravascular space though an introduction site, the introduction site being remote from the repair site;

maneuvering the second sealing stent segment, independently of the graft, through the intravascular space to the repair site;

securing the second end of the graft within a vessel at the repair site; and engaging the second sealing stent segment with the second end of the graft, thereby forming a substantially fluid-tight seal between the second end of the graft and an endoluminal surface of the vessel at the repair site.

2. The method of claim 1, the first sealing stent segment or the second sealing stent segment being a stent anastomosis.

3. The method of claim 1, the first sealing stent segment or the second sealing stent segment serving to secure the corresponding end of the graft within a vessel at the repair site.

4. The method of claim 1, the graft being maneuvered and at least one end thereof being positioned by intravascular deployment hardware passing through at least one introduction site remote from the repair site.

5. The method of claim 4, the graft being maneuvered and both ends thereof being positioned by intravascular deployment hardware passing through a single introduction site, the single introduction site being remote from the repair site.

6. The method of claim 4, the graft being maneuvered and the ends thereof being positioned by intravascular deployment hardware passing through multiple introduction sites, each of the multiple introduction sites being remote from the repair site.

7. The method of claim 1, the graft being maneuvered and at least one end thereof being positioned by extravascular deployment hardware passing through a vessel wall at the repair site.

8. The method of claim 7, both ends of the graft being positioned by extravascular deployment hardware passing through the vessel wall at the repair site.

9. The method of claim 7, the extravascular deployment hardware including at least one ligature passing through the vessel wall at the repair site.

10. The method of claim 1, at least one end of the graft being secured within the vessel by extravascular securing hardware passing through the vessel wall at the repair site.

11. The method of claim 10, the extravascular securing hardware including at least one ligature passing through the vessel wall at the repair site.

12. The method of claim 11, the ligature being tied off outside the vessel wall.

13. The method of claim 11, the ligature being retained outside the vessel wall by a sliding retainer on the ligature positioned against an outer surface of the vessel wall.

14. The method of claim 1, further comprising the step of engaging a positioning stent segment with the vessel at the repair site, the positioning stent segment being connected to one end of the graft, the positioning stent segment serving to position the connected end of the graft at the repair site.

15. The method of claim 14, the positioning stent segment serving to secure the connected end of the graft within the vessel.

16. The method of claim 14, further comprising the steps of:

disengaging from the vessel the positioning stent segment;

detaching the positioning stent segment from the connected end of the graft; and removing the positioning stent segment from the intravascular space.

17. The method of claim 1, the graft including a branch graft connected to the graft and having an open end thereof, the method further comprising:

positioning the end of the branch graft at the repair site;

inserting a third sealing stent segment, independently of the graft, into the intravascular space though an introduction site, the introduction site being remote from the repair site;

maneuvering the third sealing stent segment, independently of the graft, through the intravascular space to the repair site;

securing the end of the branch graft within a vessel at the repair site; and engaging the second sealing stent segment with the second end of the graft, thereby forming a substantially fluid-tight seal between the second end of the graft and an endoluminal surface of the vessel at the repair site.

18. The method of claim 17, the graft and branch graft being maneuvered and the ends thereof being positioned by intravascular deployment hardware passing through multiple introduction sites, each of the multiple introduction sites being remote from the repair site.

* * * * *